(12) United States Patent
Shen et al.

(10) Patent No.: US 12,285,580 B2
(45) Date of Patent: Apr. 29, 2025

(54) METHOD FOR CONVERTING INANIMATE OBJECT TO SMALL-SCALE ROBOT ON-DEMAND

(71) Applicant: City University of Hong Kong, Hong Kong (HK)

(72) Inventors: Yajing Shen, Hong Kong (HK); Xiong Yang, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 509 days.

(21) Appl. No.: 17/549,813

(22) Filed: Dec. 13, 2021

(65) Prior Publication Data

US 2022/0184360 A1 Jun. 16, 2022

Related U.S. Application Data

(60) Provisional application No. 63/124,990, filed on Dec. 14, 2020.

(51) Int. Cl.
*C09J 189/00* (2006.01)
*A61M 31/00* (2006.01)
(Continued)

(52) U.S. Cl.
CPC ............ *A61M 31/00* (2013.01); *A61M 37/00* (2013.01); *C08K 3/08* (2013.01); *C09J 129/04* (2013.01);
(Continued)

(58) Field of Classification Search
CPC .................. A61M 31/00; A61M 37/00; A61M 2037/0007; A61M 2205/0272;
(Continued)

(56) References Cited

PUBLICATIONS

X. Yang, An agglutinate magnetic spray transforms inanimate objects into millirobots for biomedical applications, Science Robotics, 5, eabc8191, p. 1-12 (Year: 2020).*
(Continued)

*Primary Examiner* — Dah-Wei D. Yuan
*Assistant Examiner* — Nga Leung V Law
(74) *Attorney, Agent, or Firm* — Idea Intellectual Limited; Margaret A. Burke; Sam T. Yip

(57) ABSTRACT

This invention provides parasitic millirobots that can effectively adapt to an unstructured environment and coherently interact with diverse objects in order to fulfil various application needs. Particularly, a minimalist millirobot construction strategy by splashing composited agglutinate magnetic spray (M-spray) is adopted, which is capable of self-turning multifarious milli-/centi-objects into parasitic millirobots on-demand. Through taking full advantage of the objects' inherent structure and a covered thin drivable film, the M-spray demonstrates superior handling (from 1-D to 3-D structures) and loading capabilities (up to thousand-fold and hundred-fold of its volume and weight, respectively) while with neglectable size increment (as low as 1%) to target. Moreover, benefitting from peculiarities of online reprogramming and controllable disintegration, the parasitic millirobots can rewrite its locomotion mode according to the task and disintegrate themselves after mission accomplished, offering high adaptivity and compatibility for in vivo biomedical applications. Methods for conversion and fabrication thereof are also provided.

7 Claims, 46 Drawing Sheets

(51) Int. Cl.
- A61M 37/00 (2006.01)
- C08K 3/08 (2006.01)
- C09J 129/04 (2006.01)
- H01F 1/06 (2006.01)
- H01F 7/02 (2006.01)

(52) U.S. Cl.
CPC .............. C09J 189/00 (2013.01); H01F 1/06 (2013.01); H01F 7/0242 (2013.01); A61M 2037/0007 (2013.01); A61M 2205/0272 (2013.01); A61M 2207/00 (2013.01); C08K 2003/0856 (2013.01); C08K 2201/01 (2013.01)

(58) Field of Classification Search
CPC .................. A61M 2207/00; C08K 3/08; C08K 2003/0856; C08K 2201/01; C09J 129/04; C09J 189/00; H01F 1/06; H01F 7/0242; H01F 1/0027; H01F 41/16; A61B 34/30
See application file for complete search history.

(56) References Cited

PUBLICATIONS

H.W. Huang, Adaptive locomotion of artificial microswimmers, Jan. 2019, Science Advances, 5, eaau1532, p. 1-7 (Year: 2019).*
Z. Zhakypov, K. Mori, K. Hosoda, J. Paik, Designing minimal and scalable insect-inspired multi-locomotion millirobots. Nature 571, 381-386 (2019).
M. Sitti, Miniature soft robots—road to the clinic. Nature Reviews Materials 3, 74-75 (2018).
K. Y. Ma, P. Chirarattananon, S. B. Fuller, R. J. Wood, Controlled flight of a biologically inspired, insect-scale robot. Science 340, 603-607 (2013).
X. Ji, X. Liu, V. Cacucciolo, M. Imboden, Y. Civet, A. El Haitami, S. Cantin, Y. Perriard, H. Shea, An autonomous untethered fast soft robotic insect driven by low-voltage dielectric elastomer actuators. Science Robotics 4, eaaz6451 (2019).
M. Cianchetti, C. Laschi, A. Menciassi, P. Dario, Biomedical applications of soft robotics. Nature Reviews Materials 3, 143-153 (2018).
H. Xie, M. Sun, X. Fan, Z. Lin, W. Chen, L. Wang, L. Dong, Q. He, Reconfigurable magnetic microrobot swarm: Multimode transformation, locomotion, and manipulation. Sci. Robot 4, eaav8006 (2019).
Y. Chen, H. Zhao, J. Mao, P. Chirarattananon, E.F. Helbling, N.S.P. Hyun, D.R. Clarke, R.J. Wood, Controlled flight of a microrobot powered by soft artificial muscles. Nature 575, 324-329 (2019).
M. Lahikainen, H. Zeng, A. Priimagi, Reconfigurable photoactuator through synergistic use of photochemical and photothermal effects. Nature communications 9, 1-8 (2018).
A. Lendlein, Fabrication of reprogrammable shape-memory polymer actuators for robotics. Science Robotics 3, eaat9090 (2018).
W. Hu, G. Z. Lum, M. Mastrangeli, M. Sitti, Small-scale soft-bodied robot with multimodal locomotion. Nature 554, 81-85 (2018).
H. Lu, M. Zhang, Y. Yang, Q. Huang, T. Fukuda, Z. Wang, Y. Shen, A bioinspired multilegged soft millirobot that functions in both dry and wet conditions. Nature communications 9, 1-7 (2018).
S. Tottori, L. Zhang, F. Qiu, K.K. Krawczyk, A. Franco-Obregon, B.J. Nelson, Magnetic helical micromachines: fabrication, controlled swimming, and cargo transport. Advanced materials 24, 811-816 (2012).
S.D. de Rivaz, B. Goldberg, N. Doshi, K. Jayaram, J. Zhou, R.J. Wood, Inverted and vertical climbing of a quadrupedal microrobot using electroadhesion. Science Robotics 3, eaau3038 (2018).
Y. Wu, J.K. Yim, J. Liang, Z. Shao, M. Qi, J. Zhong, Z. Luo, X. Yan, M. Zhang, X. Wang, R.S. Fearing, Insect-scale fast moving and ultrarobust soft robot. Science Robotics 4, eaax1594 (2019).
Y. Zhang, B. K. Chen, X. Liu, Y. Sun, Autonomous robotic pick-and-place of microobjects. IEEE Transactions on Robotics 26, 200-207 (2009).
J. Hughes, U. Culha, F. Giardina, F. Guenther, A. Rosendo and F. Iida, Soft manipulators and grippers: a review. Frontiers in Robotics and AI 3, 69 (2016).
Z. Ren, W. Hu, X. Dong, M. Sitti, Multi-functional soft-bodied jellyfish-like swimming. Nature communications 10, 1-12 (2019).
H. Gu, Q. Boehler, H. Cui, E. Secchi, G. Savorana, C. De Marco, S. Gervasoni, Q. Peyron, T.Y. Huang, S. Pane, A.M. Hirt, Magnetic cilia carpets with programmable metachronal waves. Nature communications 11, 1-10 (2020).
H.W. Huang, F.E. Uslu, P. Katsamba, E. Lauga, M.S. Sakar, B.J. Nelson, Adaptive locomotion of artificial microswimmers. Science advances 5, eaau1532(2019).
F. Ponton, C. Lebarbenchon, T. Lefèvre, D.G. Biron, D. Duneau, D.P. Hughes, F. Thomas, Parasite survives predation on its host. Nature 440, 756-756 (2006).
X. Chen, H. Yuk, J. Wu, C. S. Nabzdyk, X. Zhao, Instant tough bioadhesive with triggerable benign detachment. Proceedings of the National Academy of Sciences 117, 15497-15503 (2020).
S. Saito, S. Nobusue, E. Tsuzaka, C. Yuan, C. Mori, M. Hara, T. Seki, C. Camacho, S. Irle, S. Yamaguchi, Light-melt adhesive based on dynamic carbon frameworks in a columnar liquid crystal phase. Nature communications 7, 12094, 1-7 (2016).
G. Ju, M. Cheng, F. Guo, Q. Zhang, F. Shi, Elasticity-Dependent Fast Underwater Adhesion Demonstrated by Macroscopic Supramolecular Assembly. Angewandte Chemie International Edition 57, 8963-8967 (2018).
F. W. DelRio, M. P. de Boer, J. A. Knapp, E. D. Reedy, P. J. Clews, M. L. Dunn, The role of van der Waals forces in adhesion of micromachined surfaces. Nature materials 4, 629-634 (2005).
R. Hodge, G. H. Edward, G. P. Simon, Water absorption and states of water in semicrystalline poly (vinyl alcohol) films. Polymer 37, 1371-1376 (1996).
S. D'Amico, M. Hrabalova, U. Müller, E. Berghofer, Bonding of spruce wood with wheat flour glue—Effect of press temperature on the adhesive bond strength. Industrial Crops and Products 31, 255-260 (2010).
Y. Kim, H. Yuk, R. Zhao, S. A. Chester, X. Zhao, Printing ferromagnetic domains for untethered fast-transforming soft materials. Nature 558, 274-279 (2018).
W. Wang, J.Y. Lee, H. Rodrigue, S.H. Song, W.S. Chu, S.H. Ahn, Locomotion of inchworm-inspired robot made of smart soft composite (SSC). Bioinspiration & biomimetics 9, 046006 (2014).
J. Kim, S.E. Chung, S.E. Choi, H. Lee, J. Kim, S. Kwon, Programming magnetic anisotropy in polymeric microactuators. Nature materials 10, 747-752 (2011).
H. Markides, M. Rotherham, A. El Haj, Biocompatibility and toxicity of magnetic nanoparticles in regenerative medicine Journal of Nanomaterials 2012,Article ID 614094, (2012).
Y. Kim, G. A. Parada, S. Liu, X. Zhao, Ferromagnetic soft continuum robots. Science Robotics 4, eaax7329 (2019).
V. N. Le, N. H. Nguyen, K. Alameh, R. Weerasooriya, P. Pratten, Accurate modeling and positioning of a magnetically controlled catheter tip. Medical physics 43, 650-663 (2016).
C. Chautems, A. Tonazzini, Q. Boehler, S.H. Jeong, D. Floreano, B.J. Nelson, Magnetic continuum device with variable stiffness for minimally invasive surgery. Advanced Intelligent Systems 2, 1900086 (2020).
B.E.F. de Àvila, P. Angsantikul, J. Li, M.A. Lopez-Ramirez, D.E. Ramirez-Herrera, S. Thamphiwatana, C. Chen, J. Delezuk, R. Samakapiruk, V. Ramez, M. Obonyo, Micromotor-enabled active drug delivery for in vivo treatment of stomach infection. Nature communications 8, 1-9 (2017).
Y. Alapan, U. Bozuyuk, P. Erkoc, A. C. Karacakol, M. Sitti, Multifunctional surface microrollers for targeted cargo delivery in physiological blood flow. Science Robotics 5, eaba5726(2020).
Xiong Yang et al., An agglutinate magnetic spray transforms inanimate objects into millirobots for biomedical applications. Science Robotics 5, eabc8191(2020).

* cited by examiner

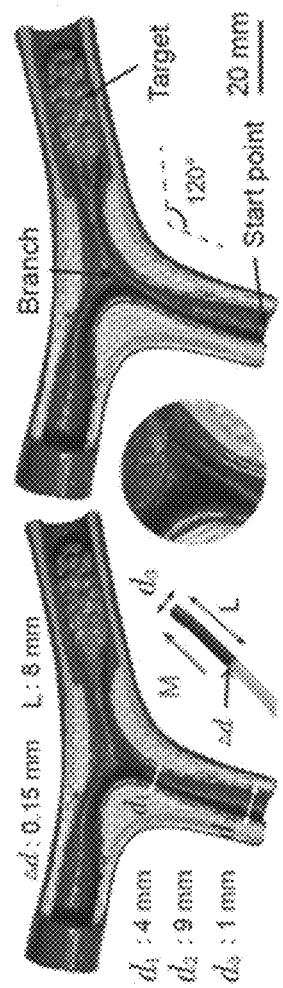
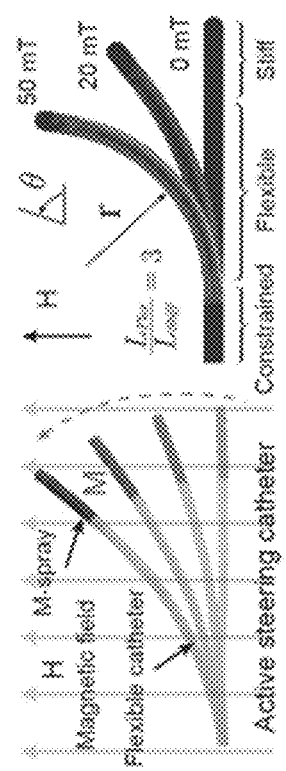
FIG. 6A
FIG. 6B

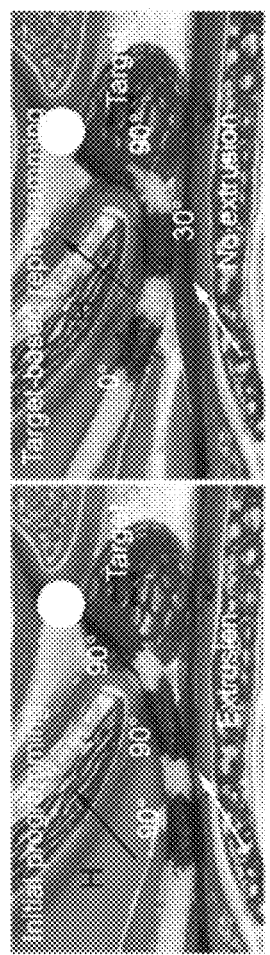
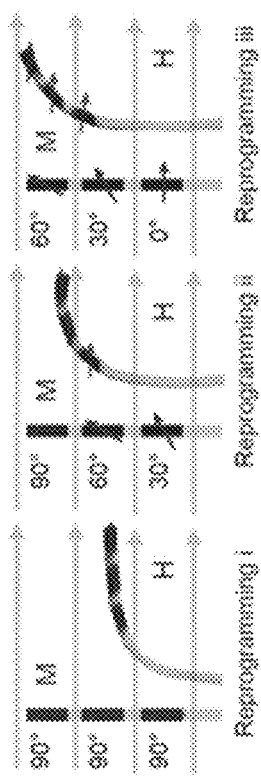
FIG. 6C
FIG. 6D

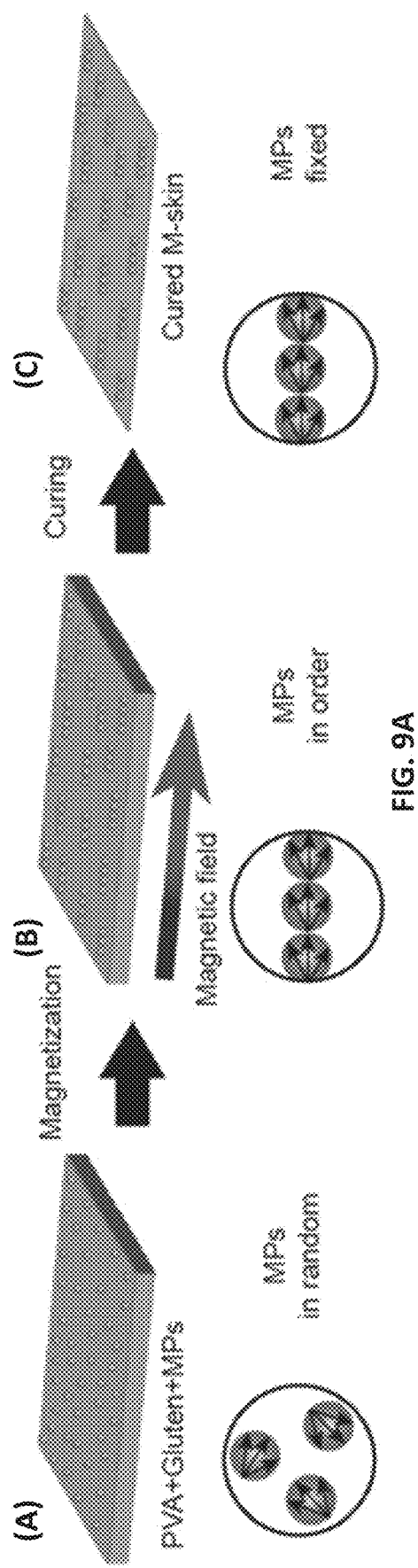
FIG. 9A
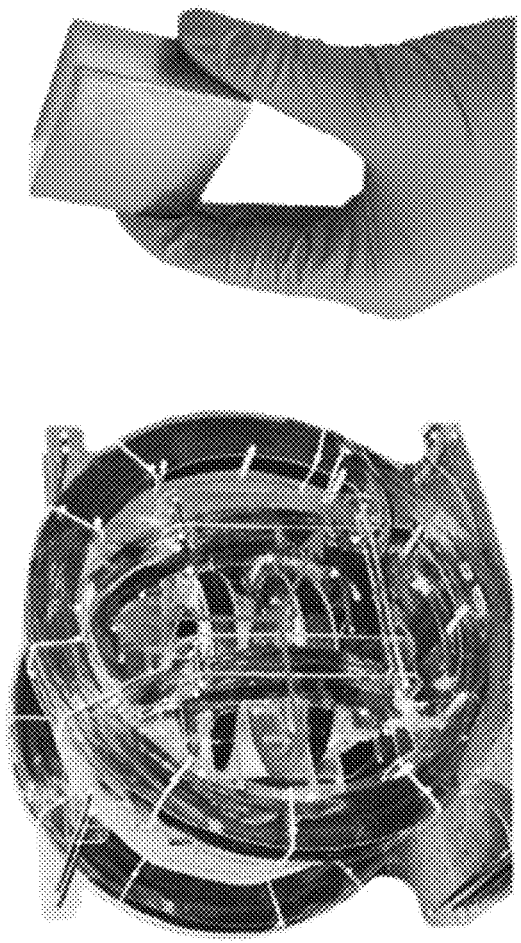
FIG. 9B
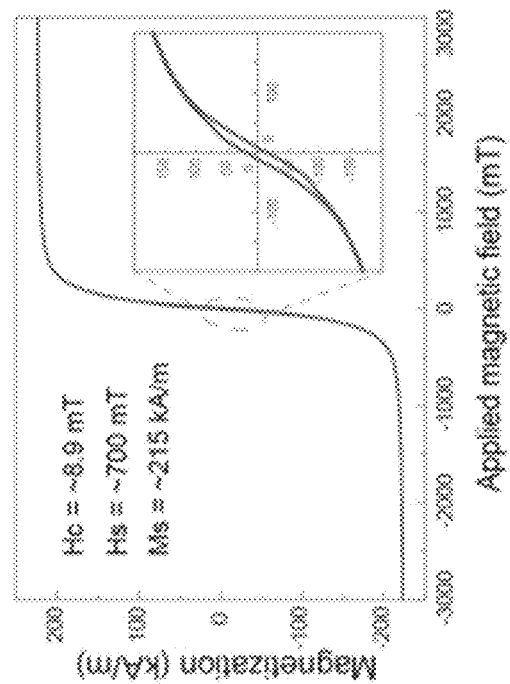

METHOD FOR CONVERTING INANIMATE OBJECT TO SMALL-SCALE ROBOT ON-DEMAND

CROSS-REFERENCE WITH RELATED APPLICATIONS

The present application claims priority from the U.S. Provisional Patent Application No. 63/124,990 filed Dec. 14, 2020, and the disclosure of which is incorporated herein by reference in its entirety.

FIELD OF THE INVENTION

The present invention relates to a method for converting inanimate target objects of one-dimensional (1-D) to three-dimensional (3-D) configurations into parasitic millirobots, with programmable actuation direction as well as controllable magnetic induced disintegration. The present invention also relates to parasitic millirobots having such convertibility on-demand, methods of fabrication and using the millirobots in a wide variety of applications.

BACKGROUND

Insect-scale robots (or millirobots) may find use in biomedical, exploration, and other emerging applications that require distinct controllability, adaptability, safety, and integrity (1-5). Recent progress in materials has enabled smart actuators with different driving mechanisms, such as magnetic fields, biohybrid artificial muscles, photochemical/photothermal effects, shape-memory polymers, etc. (6-9). By introducing biomimetic design (e.g., helix, legged, jellyfish, etc.), those milli-actuators can be formed into millirobots that realize effective locomotion and perform complex tasks in harsh environments (10-14). However, the in-depth inter-action between the constructed millirobot and the operated target remains a challenge due to the target's arbitrary size and unstructured shape and unpredictable, limited working space in practice.

Conventionally, traditional robots are designed together with an extra dexterous end effector (15, 16) to interact with the object, e.g., picking, placing, transportation, etc. Limited by energy supply and finite working space, it can be challenging to adopt additional end-effector design to implement tasks at small scale. Nowadays, the usage of soft materials blurs the boundary between robot body and end effector to some extent, allowing a millirobot to be a whole unit for object operation, which greatly reduces the robot's size and enhances flexibility, efficiency, and safety (10, 17, 18). However, to fulfil the in-depth interaction between the millirobot and the un-structured targets at small scale, at least two key challenges must be taken into consideration: unmodifiable structure after fabrication and target size increment. Benefitting from the attributes of soft materials, such as polydimethylsiloxane (PDMS), Ecoflex, hydro-gels, and so on, existing soft millirobots can achieve changeable morphology. However, after fabrication, the inherent structure of the robot is fixed, and its deformability is limited to a few statuses, e.g., compression, stretch, or curl (19). Therefore, it is difficult to design one robot that can adapt to diverse objects with various structures and shapes. Furthermore, even if the millirobot can successfully handle the object, the size increment superposed to the target may be difficult in practice, especially when such operations (e.g., exploration and target delivery) are implemented in a narrow space. These inherent issues essentially challenge the existing materials and robotics, adding more requirements to a coherent robot-object interaction strategy and the corresponding robot design concept in the meantime.

An adhesion strategy could be adapted to most target surfaces irrespective of the specific shape or size of the targets. Recently, scientists have developed diverse adhesive materials and applied them to tissue adhesion and self-healing, as well as engineering applications, such as the instant tough bio tape from the combination of polyvinyl alcohol (PVA) and poly(acrylic acid) (20), the reusable light-melt adhesion by dynamic carbon frameworks in liquid crystal (27), and fast underwater adhesion based on macroscopic supramolecular assembly (22). The progress in adhesive material development and adhering strategy in nature provides some insights in designing a new millirobot to achieve the effective robot-object interaction at small scale.

SUMMARY OF THE INVENTION

Accordingly, a minimalist millirobot construction approach is herein adopted, which is intended to transform inanimate objects into millirobots by coating a target's surface with a highly adhesive and wettable spray composition for converting inanimate objects into small-scale robots (e.g., millirobots), which can adhere to a wide variety of surfaces including, but not limited to, 1-D, 2-D, or 3-D objects, and with a covered film (e.g., about 100 to 250 µm) that is thin enough to preserve the target's original size, morphology, and structure. Under actuation of magnetic field, the constructed millirobots are able to demonstrate a range of locomotive abilities including, but not limited to, crawling, walking, and rolling. This approach offers a general on-demand robot construction method by leveraging the structure and morphology of the targeted objects themselves and may find a wide range of applications in biomedical engineering.

In a first aspect, the present invention provides a self-adhesive, highly viscous and wettable spray composition for fabricating one or more small-scale robots from one or more inanimate objects of one-dimensional to three-dimensional configurations on-demand, where the composition includes, but not limited to:
  one or more curable adhesive materials; and
  a plurality of drivable materials,
  where the one or more curable adhesive materials, upon exposure to one or more stimuli, form a highly viscous paste to splash in one or more splashing regions on a surface of a substrate with which the composition is in contact, and after the composition is cured, further increase mechanical strength of the cured composition while preventing detachment of the cured composition from the substrate;
  the plurality of drivable materials, upon exposure to one or more stimuli and prior to curing of the composition, are aligned to have an oriented actuation direction either perpendicularly to a deformable direction of the one or more small-scale robots or in parallel to a longest planar axis of a drivable thin film formed on the substrate surface from the cured composition.

In one embodiment, the one or more curable adhesive materials include one or more adhesive polymers to form a highly viscous polymer paste.

In one embodiment, the one or more drivable materials include a plurality of magnetic-responsive metal particles being aligned to have the oriented magnetization axis by magnetic field.

In some embodiments, a first adhesive polymer, the plurality of magnetic-responsive particles and a second adhesive polymer are in a mass ratio of 1:8:11.

In some embodiments, the first adhesive polymer and the plurality of magnetic-responsive particles are doped into a solution of the second adhesive polymer at room temperature, followed by atomization into droplets for forming the drivable thin film in the one or more splashing regions on the surface of the substrate with the one or more inanimate objects.

In a specific embodiment, the first adhesive polymer is gluten.

In another specific embodiment, the second adhesive polymer is polyvinyl alcohol In other specific embodiment, the magnetic-responsive particles are iron particles.

In certain embodiments, the substrate includes, but not limited to, polydimethylsiloxane, glass, paper, plastic, and wood; the surface of the substrate is flat, curved, or irregular.

In some preferred embodiments, the magnetic-responsive particles are aligned under exposure to an initial magnetic field such that the drivable thin film with the oriented magnetization axis is formed on the surface of the one or more inanimate objects on the substrate.

In a specific embodiment, the initial magnetic field is in a magnitude of about 100 to 200 mT.

A second aspect of the present invention provides a method of fabricating one or more small-scale robots from one or more inanimate objects of one-dimensional to three-dimensional configurations on-demand, where the method includes:
  splashing the composition of the first aspect in one or more splashing regions on a surface of a substrate of the one or more inanimate objects at room temperature, where areas other than the splashing regions on the surface of the substrate are masked if there is more than one splashing region;
  applying one or more stimuli to the composition to align the one or more drivable materials to have an oriented actuation direction parallel to the direction of the applied initial stimuli;
  curing the composition to form the drivable thin film with an oriented actuation direction either perpendicular to a deformable direction of the one or more small-scale robots or parallel to a longest planar axis of the drivable thin film,
  in which for the substrate surface with more than one splashing region the one or more small-scale robots are obtained by repeating said splashing, applying the initial stimuli to the composition, and curing the composition until all the splashing regions are cured followed by cutting the unmasked areas out from the substrate.

In one embodiment, the composition includes a first adhesive polymer, the one or more drivable materials including a plurality of magnetic-responsive particles, and a second adhesive polymer which are in a mass ratio of 1:8:11.

In a specific embodiment, the first adhesive polymer and the plurality of magnetic-responsive particles are doped into a solution of the second adhesive polymer at room temperature, followed by atomization into droplets for forming a thin film on the substrate of the inanimate objects.

In one embodiment, the first adhesive polymer is gluten.

In another embodiment, the second adhesive polymer is polyvinyl alcohol

In other embodiment, the magnetic-responsive particles are iron particles.

In certain embodiments, the substrate includes, but not limited to, polydimethylsiloxane, glass, paper, plastic, and wood, and the surface of the substrate is flat, curved, or irregular.

In one embodiment, one of the stimuli is a magnetic field in a magnitude of about 100 to 200 mT.

A third aspect of the present invention provides a method for converting one or more inanimate objects into small-scale robots on-demand in order to exert a diversity of locomotion in an unstructured environment, where the method includes:
  providing the one or more inanimate objects with a drivable thin film formed from the composition in any of the above aspects or described herein under exposure to the initial stimuli encapsulating the one or more inanimate objects.

In one embodiment, the method further includes:
  reprogramming topology order of the one or more drivable materials including a plurality of magnetic-responsive particles in the drivable thin film such that an initial oriented magnetization axis of the magnetic-responsive particles is re-aligned to a different orientation under a subsequent exposure to a second magnetic field which is stronger than the first magnetic field; and
  magnetically disintegrating the drivable thin film from the one or more small-scale robots under exposure to an oscillating magnetic field.

In one embodiment, the second magnetic field is about 200 mT or more, and is applied in a direction perpendicular to that of the initial magnetic field during formation of the drivable thin film, and wherein said topology order of the plurality of the magnetic-responsive particles is reprogrammed by wetting the drivable thin film so that spacing between each of the plurality of magnetic-responsive particles in the drivable thin film increases before being exposed to the second magnetic field.

In a specific embodiment, the oscillating magnetic field applied to the one or more small-scale robots has an oscillating frequency of about 1 to 3 Hz in a magnitude of about 10 mT for about 2 to 4 minutes.

BRIEF DESCRIPTION OF THE DRAWINGS

Embodiments of the invention are described in more details hereinafter with reference to the drawings, in which:

FIG. 6A schematically depicts active steering catheter constructed by M-spray coating and its deformation model under magnetic fields with different strengths;

FIG. 6B schematically depicts the navigation ability of the one-point catheter in a narrow vascular model;

FIG. 6C schematically depicts the reprogramming of multi-point sampling cotton thread for various sets of active steering catheter;

FIG. 6D shows reprogramming of the easy magnetization axis of multi-point sampling cotton thread according to the corner angle of the throat, which can achieve the fast directional steering under the actuation of magnetic torque and can reduce the risk of extrusion with throat wall during insertion;

FIG. 9A with labels (A), (B), and (C) shows the curing process and magnetic property of M-spray and FIG. 9B shows the equipment used for magnetic field production;

DETAILED DESCRIPTION OF THE INVENTION

In the following description, systems and methods for and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

It should be apparent to practitioner skilled in the art that the foregoing examples of the system and method are only for the purposes of illustration of working principle of the present invention. It is not intended to be exhaustive or to limit the invention to the precise forms disclosed.

Raw Materials of M-Spray

The PVA with 87.0 to 89.0% degree of alcoholysis was bought from Aladdin Chemistry Co. Ltd. Gluten (wheat protein) was obtained from Mingzuotang fishing tackle Corporation. Iron micropowder [Spherical, aerodynamic particle sizer (APS) 6 to 10 μm, reduced, 99.5%] was purchased from Alfa Aesar. Water with a resistivity of 18.2 megoh surface, which is mainly caused by the larger bonding force of hydrogen bonds than the van der Waals force as discussed above.

Figure 2A:
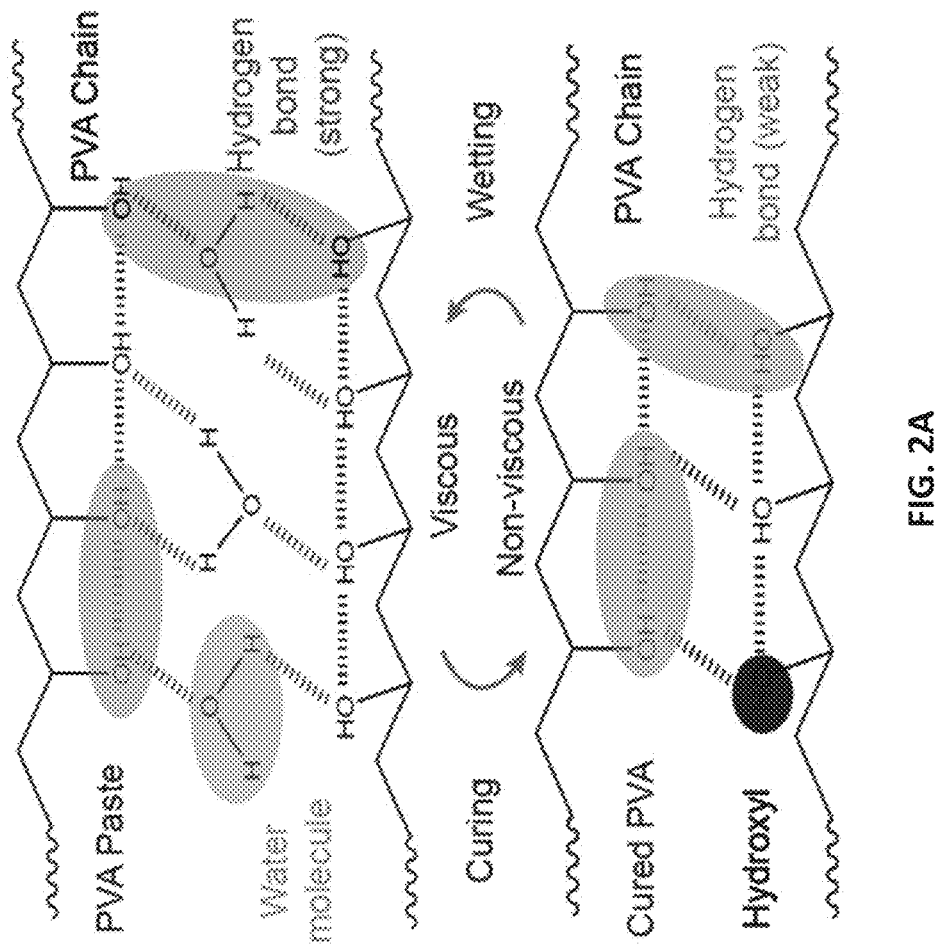
FIG. 2A schematically depicts the state change of the M-spray between viscous and nonviscous forms.
Figure 2B:
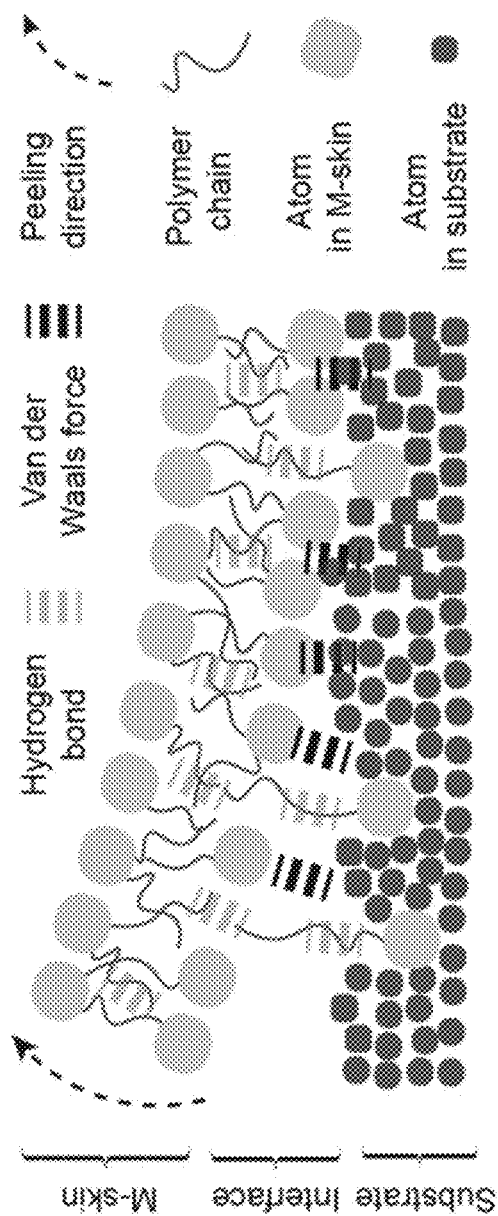
FIG. 2B schematically depicts the bonding force between cured M-skin and substrate surface during the peeling process.
Figure 2C:
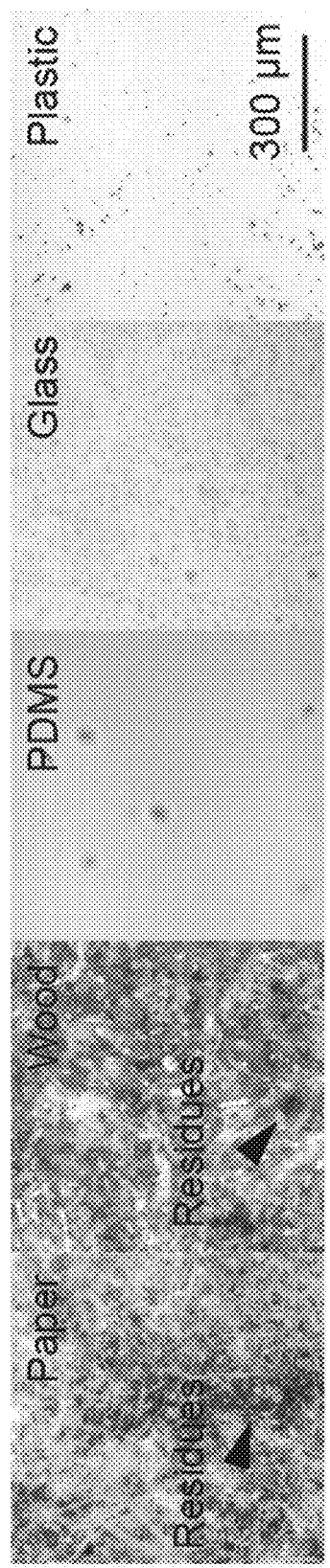
FIG. 2C shows a series of optical microscopy images of the contact surface on testing materials after the M-skin is peeled off.
Figure 2D:
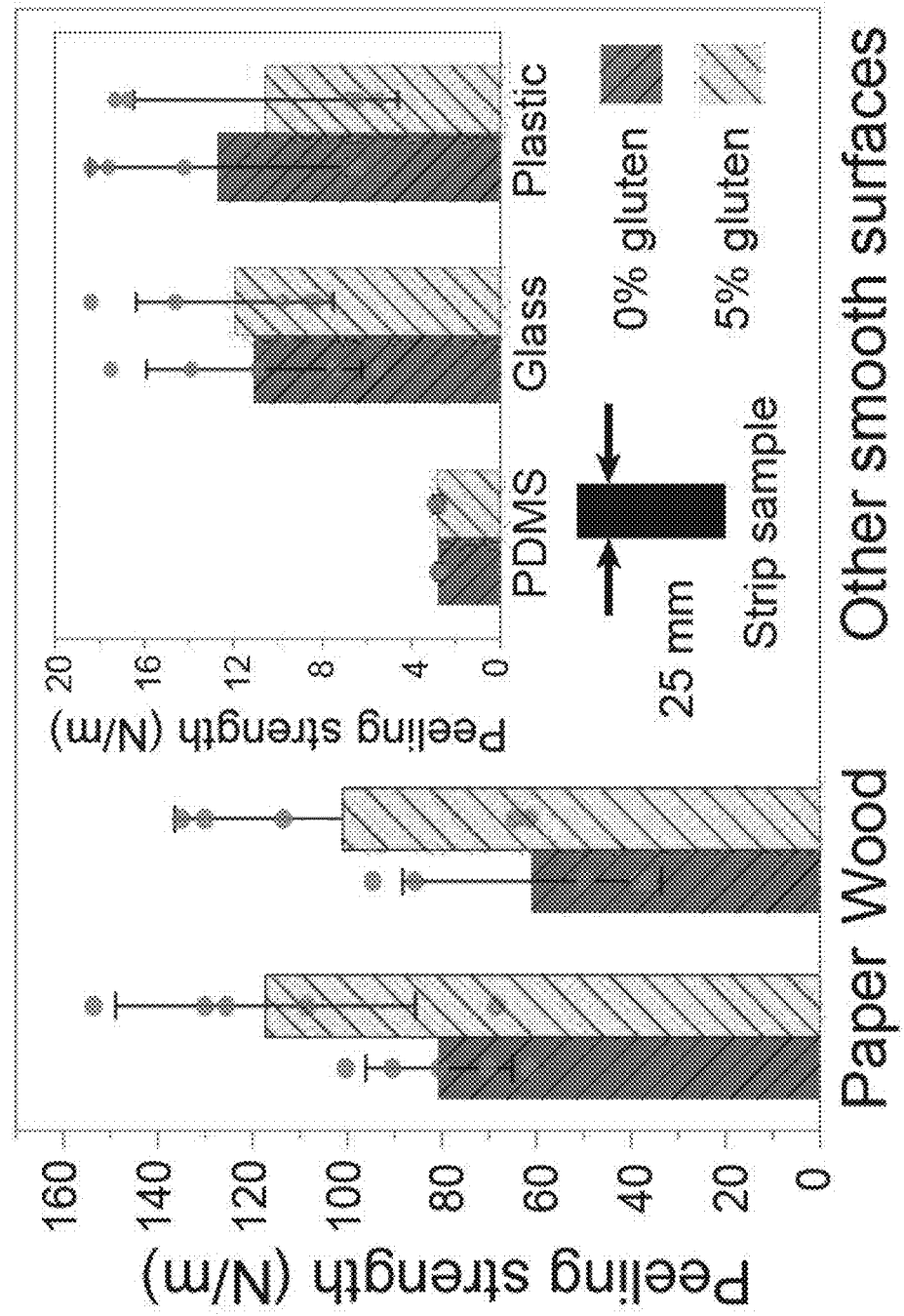
FIG. 2D shows quantitative peeling strength of the M-skin to rough (paper and wood) and smooth surfaces (PDMS, glass, and plastic); error bars indicate the SD for n=5 measurements at each data point.
Figures 2E, 2F:
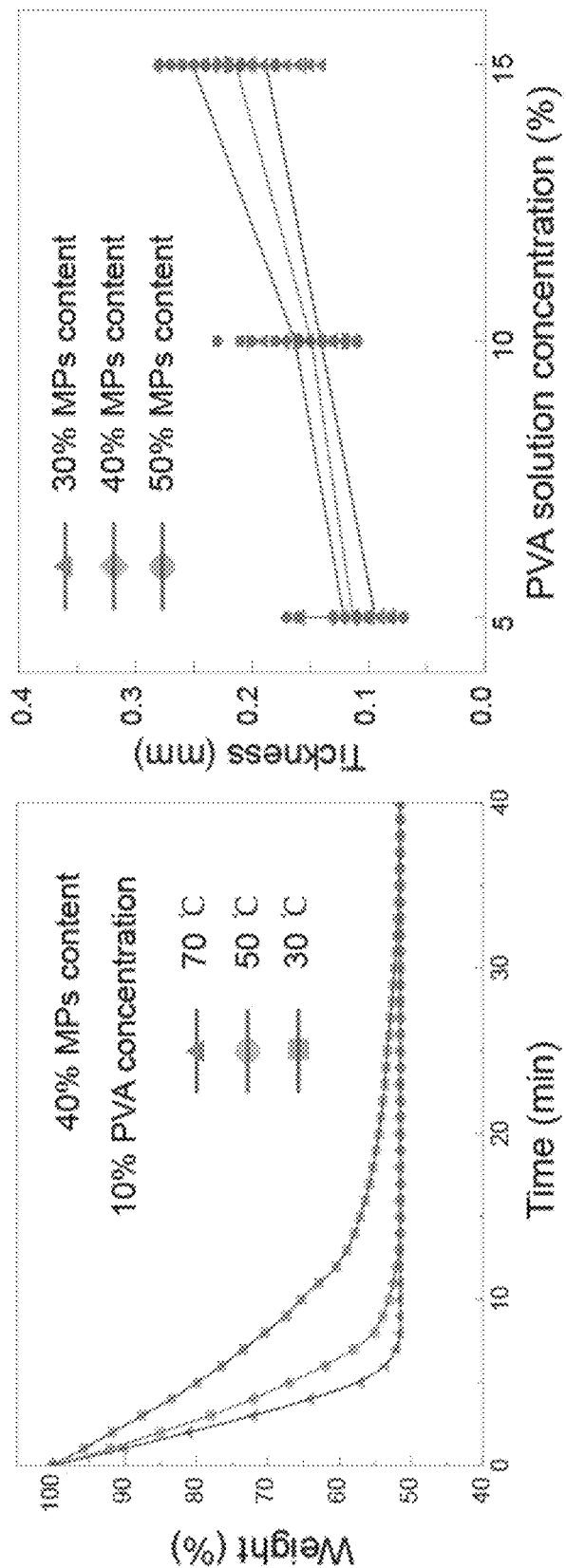
FIG. 2E shows the curing rate of the M-spray at different environment temperatures.
FIG. 2F shows the effect of magnetic particles (MP) content and PVA solution concentration on the final thickness of the M-skin; error bars indicate the SD for n=10.

To further understand the paste-solid transition of M-spray, the effects of temperature, MP content, and PVA solution concentration on the curing process were studied by contrast experiments. FIG. 2E presents the weight change of the M-spray with 40% MP content in the curing process, indicating that higher temperature would greatly speed up the paste-solid transition process. In FIG. 2E, the transition time was shortened from ~30 min at 30° C. to ~5 min at 70° C. due to the faster water evaporation. It is found that the final structure and size of the M-skin is not relevant to the curing speed, suggesting that a faster on-demand construction is achievable by accelerating the paste-solid transition, such as higher temperature, lower humidity, or enhanced air convection. On the other hand, the thickness of M-skin is found to be relevant to the MP content and PVA solution concentration (FIG. 2F). Particularly, it decreased nearly threefold (from 251 to 94 μm) when the MP content decreases from 50 to 30% and the PVA solution concentration was adjusted from 15 to 5%, which could provide guidance for adjusting the M-skin's thickness.

The Magnetization Characterization of M-Skin

Figure 1A:
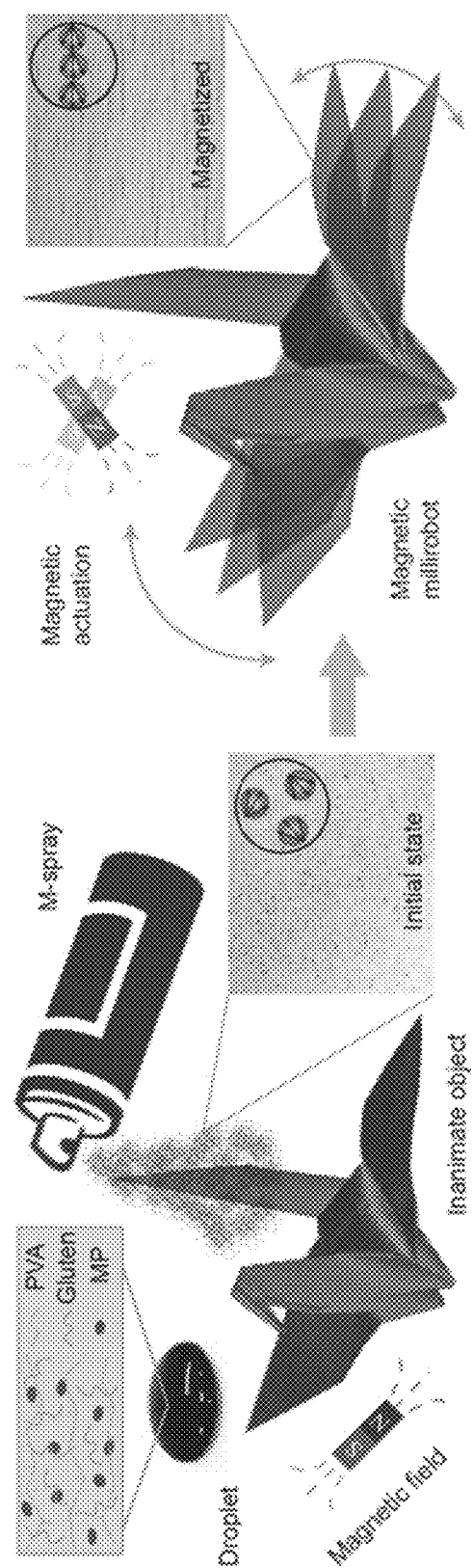
FIG. 1A schematically depicts the M-spray turns an origami crane into a magnetic millirobot according to an embodiment of the present invention.
Figures 1B, 1C:
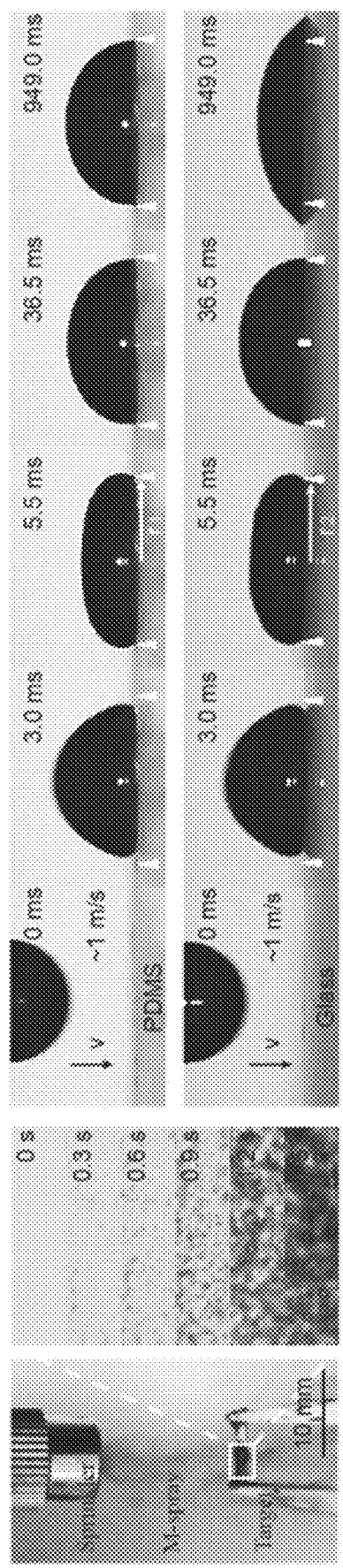
FIG. 1B shows a coating of the present M-spray from a pressurization watering can.
FIG. 1C illustrates the adhesion process of the M-spray droplets on PDMS and glass surface by a series of photographs; droplets adhere to the substrate stably and firmly without bounce or lateral migration.
Figure 1D:
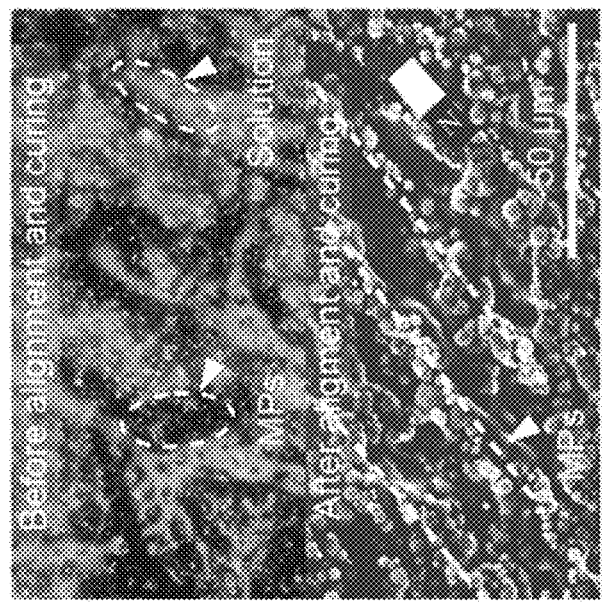
FIG. 1D shows a surface texture of the M-skin before and after alignment and curing.

To endow the controllable actuation, the random MPs in the agglutinate M-spray composition were aligned into orientated chains by applying a ~100-mT directional magnetic field, in which the formed magnetic chains tend to coincide with the magnetic field lines. After thermal curing, a thinner, solidified magnetic film (~100 to 250 μm) with an oriented easy magnetization axis was obtained on the surface of the inanimate object in several minutes, namely magnetic skin, or M-skin for short (FIG. 1D and FIG. 9A with labels (A), (B), (C) and FIG. 9B).

Figures 1E, 1F:
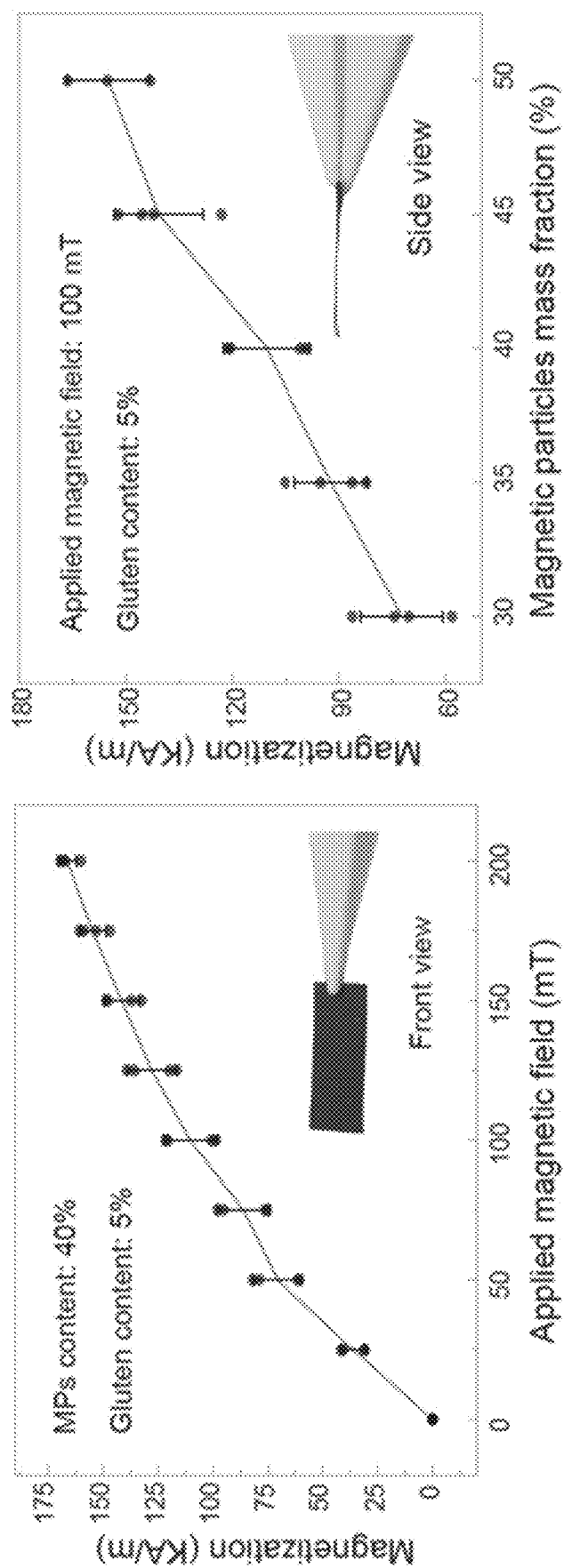
FIG. 1E shows magnetic susceptibility of the cured M-skin with 40% mass fraction of MPs when the applied magnetic field strength is from 0 to 200 mT.
FIG. 1F shows magnetic susceptibility of the cured M-skin corresponding to various MP content from 30 to 50 wt. % under 100 mT; error bars indicate the SD for n=4 measurements at each data point.
Figure 10:
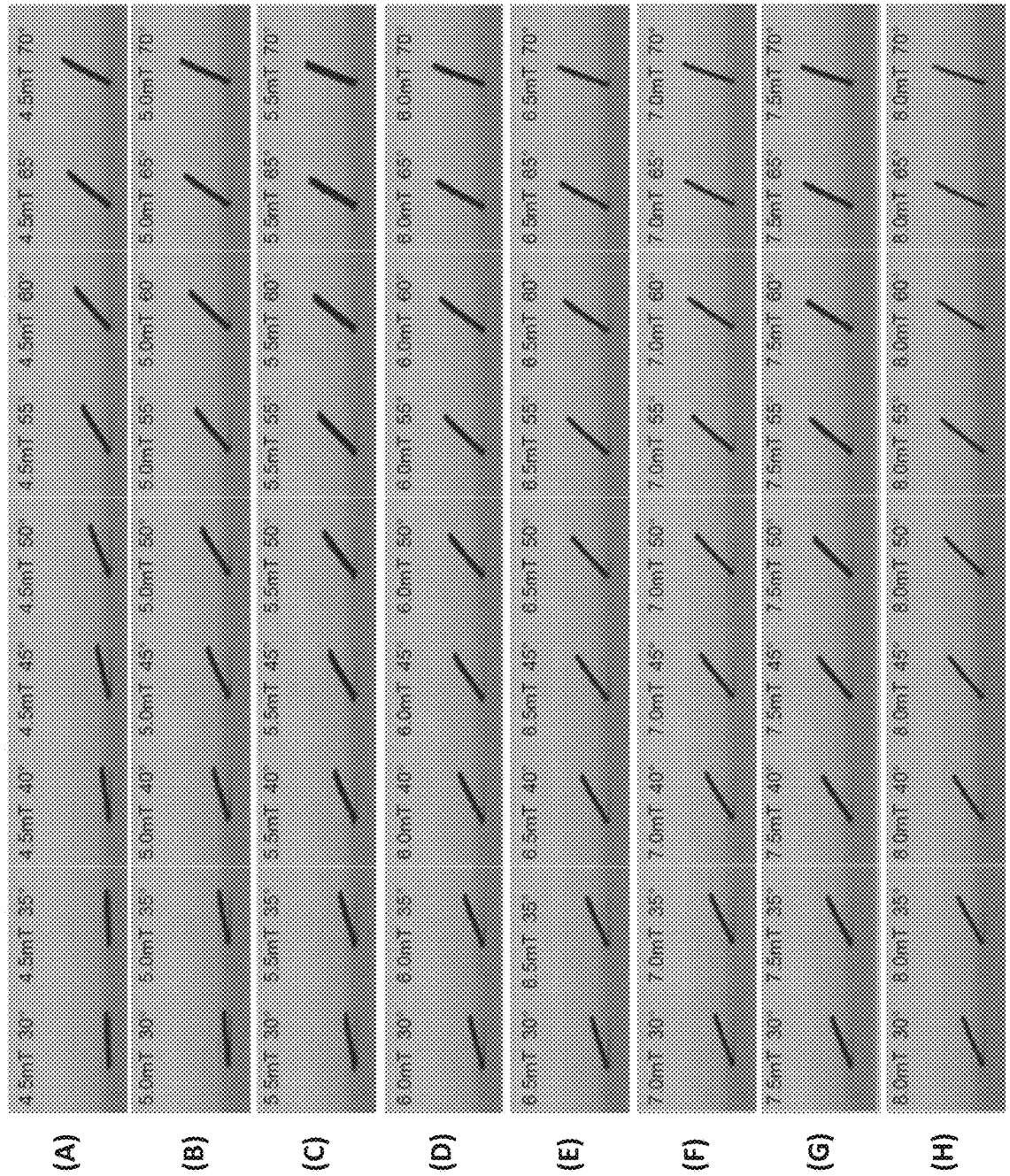
FIG. 10 with labels (A), (B), (C), (D), (E), (F), (G), (H) shows the actuating performance of the M-skin under magnetic field.
Figure 11B:
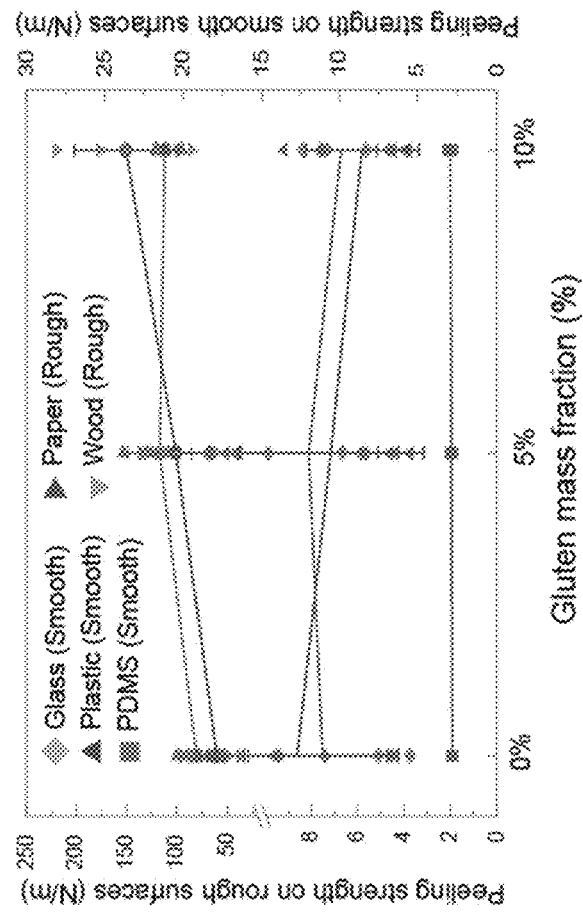
FIG. 11A and FIG. 11B show the mechanical properties and adhesiveness of the cured M-spray.
Figure 11A:
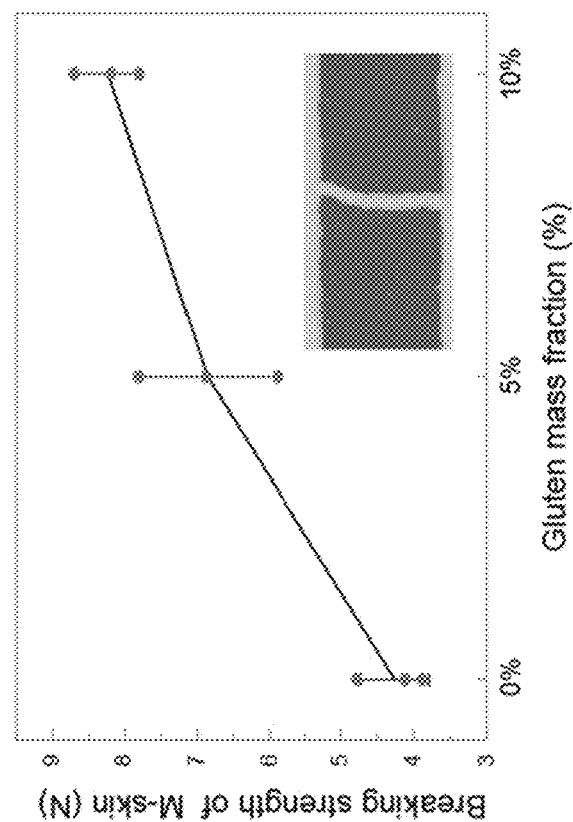

To quantitively evaluate the magnetization (magnetic moment density) of M-skin under different magnetic field strengths and MP mass fractions, the M-skin in a dimension of 10 mm by 10 mm by 0.2 mm was peeled off from the substrate carefully and its magnetization was measured by a vibrating sample magnetometer (DMS 1660, ADE Technologies) (FIGS. 1E and 1F). The results indicate that the M-skin with 40% MPs mass fraction exhibited a nearly linear increase in magnetization from 0 to 166.1 kA/m with an increase in the applied magnetic field from 0 to 200 mT (FIG. 1E). In addition, the magnetization also almost linearly increased from 72.2 to 154.9 kA/m corresponding to the increment of MP mass fraction from 30 to 50% while keeping the applied magnetic field at about 100 mT (FIG. 1F). This directional and controllable actuating capability of M-skin (FIG. 10 with labels (A), (B), (C), (D), (E), (F), (G), (H)) made it possible to turn inanimate objects into magnetic millirobots.

The Peeling Strength Test of M-Spray to Different Materials

The combining force between the M-spray and inanimate objects was evaluated by the peeling strength. In the test, the M-spray was daubed as a strip (25 mm by 50 mm) on the surface of different testing objects, including standard A4 paper (Double A, premium), wood (Cedar), PDMS (0.1 equivalent curing agents, Sylgard 184, Dow Corning), glass slide (catalog no. 7107, Sail brand), and plastic sheet (polyethylene). After the evaporation of excess water, the cured M-spray was peeled off along the long axis direction at a constant speed of 2.5 mm/s. The dynamometer (ELK-20, 0.01 N precision, Elecall Corporation) was used to obtain the average force during the peeling process.

The Fabrication Process of the M-Skin Millirobots

Figure 13A:
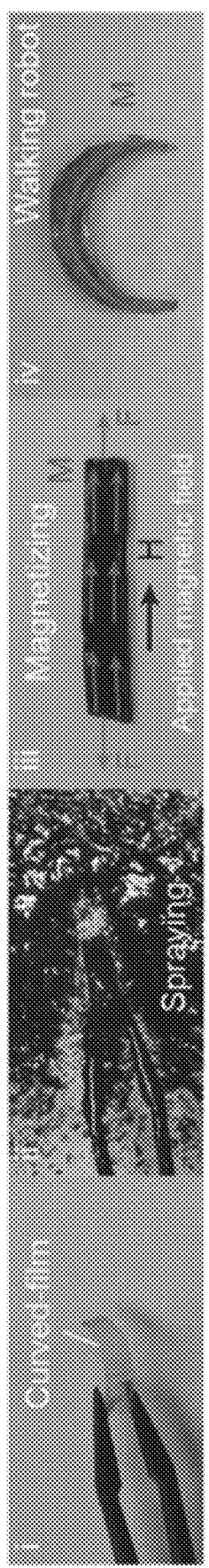
FIG. 13A, FIG. 13B, FIG. 13C, and FIG. 13D show the construction process of M-skin millirobots.
Figure 13B:
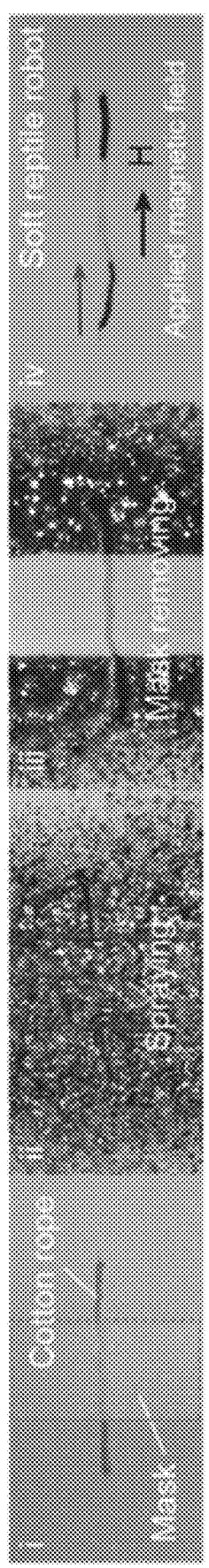
Figure 13C:
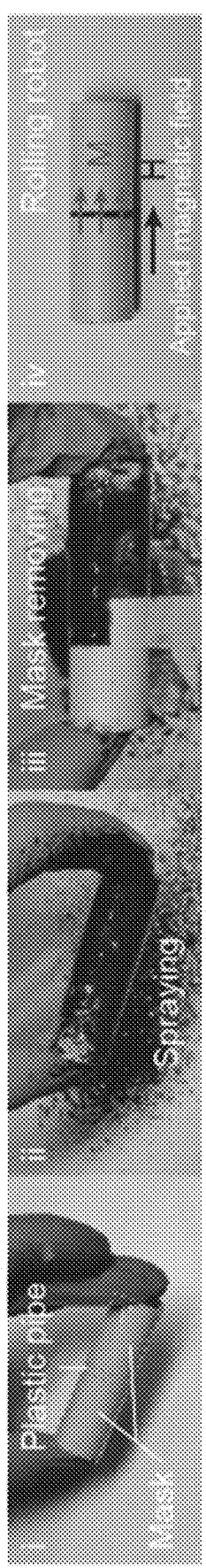

In general, the fabrication of the M-skin millirobot followed the same coating, magnetizing, and curing process. For a fully coated walking robot (FIG. 13A), the M-spray was first coated on a curved PDMS film and then stretched it to a plane and magnetized at about 100 mT along the long axis during the curing process. After curing, the walking robot was obtained by recovering the PDMS film to curve. For the soft reptile robot and rolling robot, which were partly coated (FIG. 13B and FIG. 13C), a mask was used to protect the unselected region before coating M-spray. Then, the magnetic field with a strength of 100 mT was adopted to magnetize the robot with a single magnetization direction during curing. Last, the designed reptile robot and rolling robot could be obtained after curing.

Figure 13D:
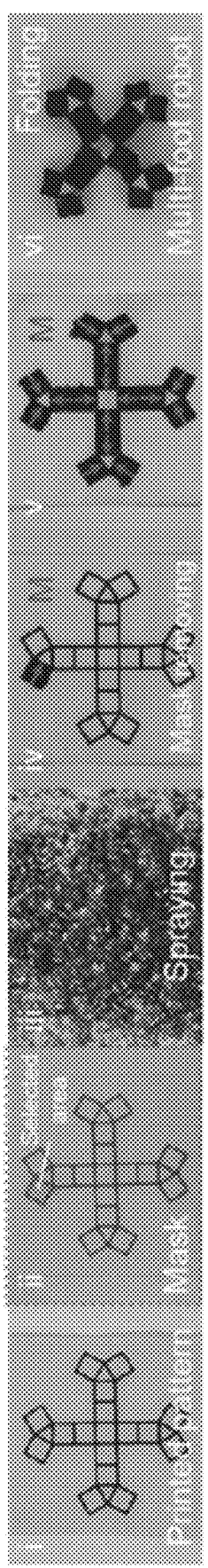

The multi-foot origami robot (FIG. 13D) was constructed with multiple partial coats and with multiple magnetization directions. First, the designed pattern was printed on the paper as the substrate of the constructed origami robot. Second, the mask with a designed penetrable area was used to select the first coating region. After the spraying, magnetizing, and curing, the first coating region was obtained. Then, other regions with the mask were selected and the spraying, the magnetizing, and curing were repeated. Last, the magnetic multi-foot origami robot was obtained by cutting and folding the substrate.

Disintegration Evaluation of M-Skin

The cured M-skin in still water could maintain stability but become disintegrable after applying magnetic agitation generated by the Helmholtz coil system. Here, the disintegration rate was defined as the ratio between the area of fragmentation and the original area of M-skin. Fragmentations with a size smaller than 2.5% of the origin area were considered as disintegrated. For the disintegration analysis of free M-skin, the size of M-skin was 5 mm by 5 mm, and the applied magnetic field had a strength of 10 mT and frequency from 0 to 5 Hz. To investigate the influences of different substrate surfaces on the M-skin disintegration, the M-spray with the same size of 5 mm by 5 mm was daubed to the different material substrates (table 1) under an applied magnetic field with a strength of 10 mT and a frequency of 1 Hz.

TABLE 1

| Substrates used in the M-skin disintegration testing: | | | |
|---|---|---|---|
| Materials | Size (mm$^3$) | Weight (g) | Remarks |
| Wood | 10 × 10 × 5.0 | 0.4643 | Cedar |
| Paper | 10 × 10 × 0.1 | 0.0085 | A4 paper |
| PDMS | 10 × 10 × 0.7 | 0.0632 | 0.1 equivalent curing agents |
| Glass | 10 × 10 × 1.0 | 0.2681 | CAT. NO. 7107, Sail brand |
| Plastic | 10 × 10 × 0.3 | 0.0323 | Polyethylene |

In Vivo Model Setup

This test aims to collect basic evidence for drug delivery function of the proposed millirobot in live animals. Four 8- to 12-week-old male New Zealand rabbits, weighing 1.8 to 2.1 kg, were obtained from Shenzhen Advanced Medical Services Co. Ltd. and randomly divided into four groups. No animal was excluded from this study. All rabbits underwent 8 hours of fasting treatment before the experiment. Both water feeding and anesthesia were maintained during the whole experiment process. Experiment group 1 was treated by oral administration of the constructed M-skin capsules containing 1.0-g glass bead particles (500 μm), and the same glass beads without M-skin capsules were orally delivered to control group 1. Experiment 2 was treated by the constructed M-skin capsules containing 0.05-g biological stain (Indigo carmine, Phygene Scientific, PH9195), and control group 2 was given the same amount of stain without M-skin capsules by oral delivery. The locomotion of M-skin capsule was achieved by magnetic field, and its position was detected by radiology imaging (DSA, CGO-2100, Wandong). Because of the harmfulness of radiology imaging, the magnetic actuation and imaging were conducted at intervals. After half an hour, the retention of glass beads in vivo (control group 1 and experiment group 1) was evaluated by ultrasound imaging (Philips EPIQ 7 ultrasound system), and the diffusion of biological stain (control group 2 and experiment group 2) was observed by collecting the stomachs after euthanasia.

Principle of Turning Inanimate Objects into Millirobots

Figure 3A:
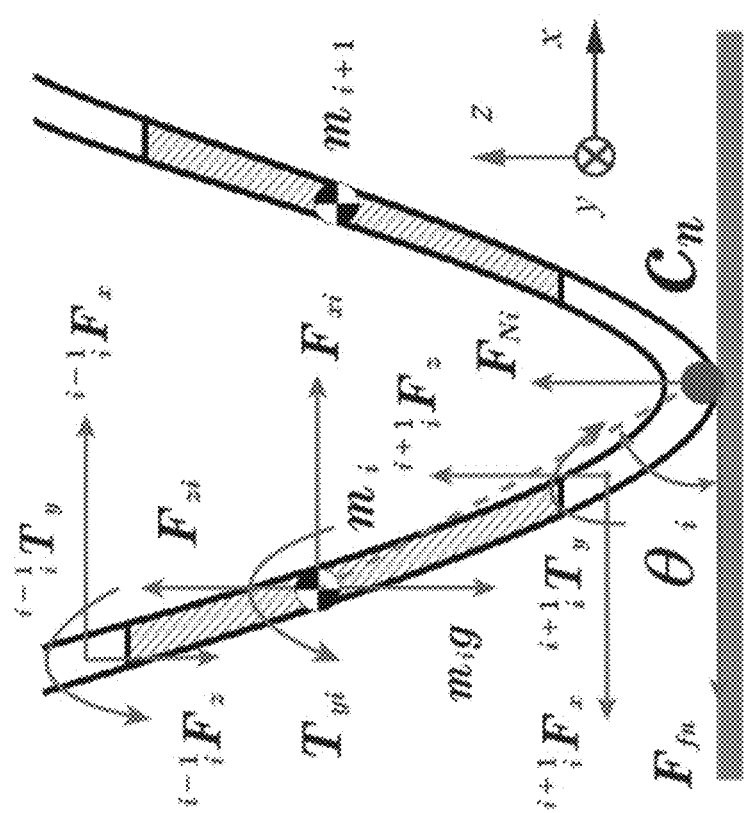
FIG. 3A schematically depicts the enlarged part of the robot's single anchor for general mechanical analysis.
Figure 12A:
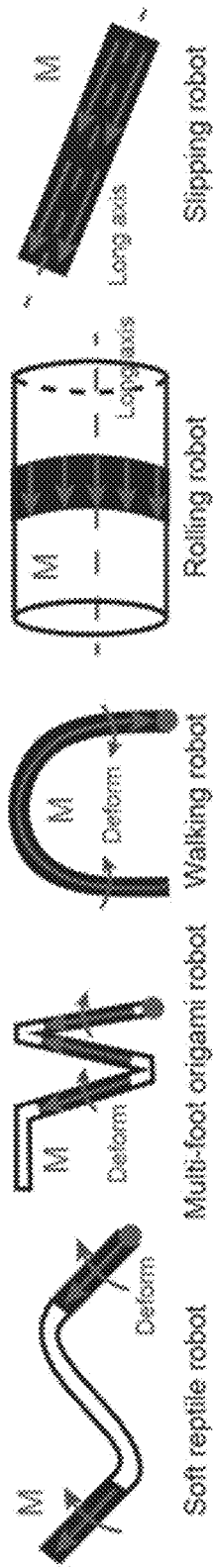
FIG. 12A and FIG. 12B show the design and locomotion analysis of diverse M-skin millirobots.
Figure 12B:
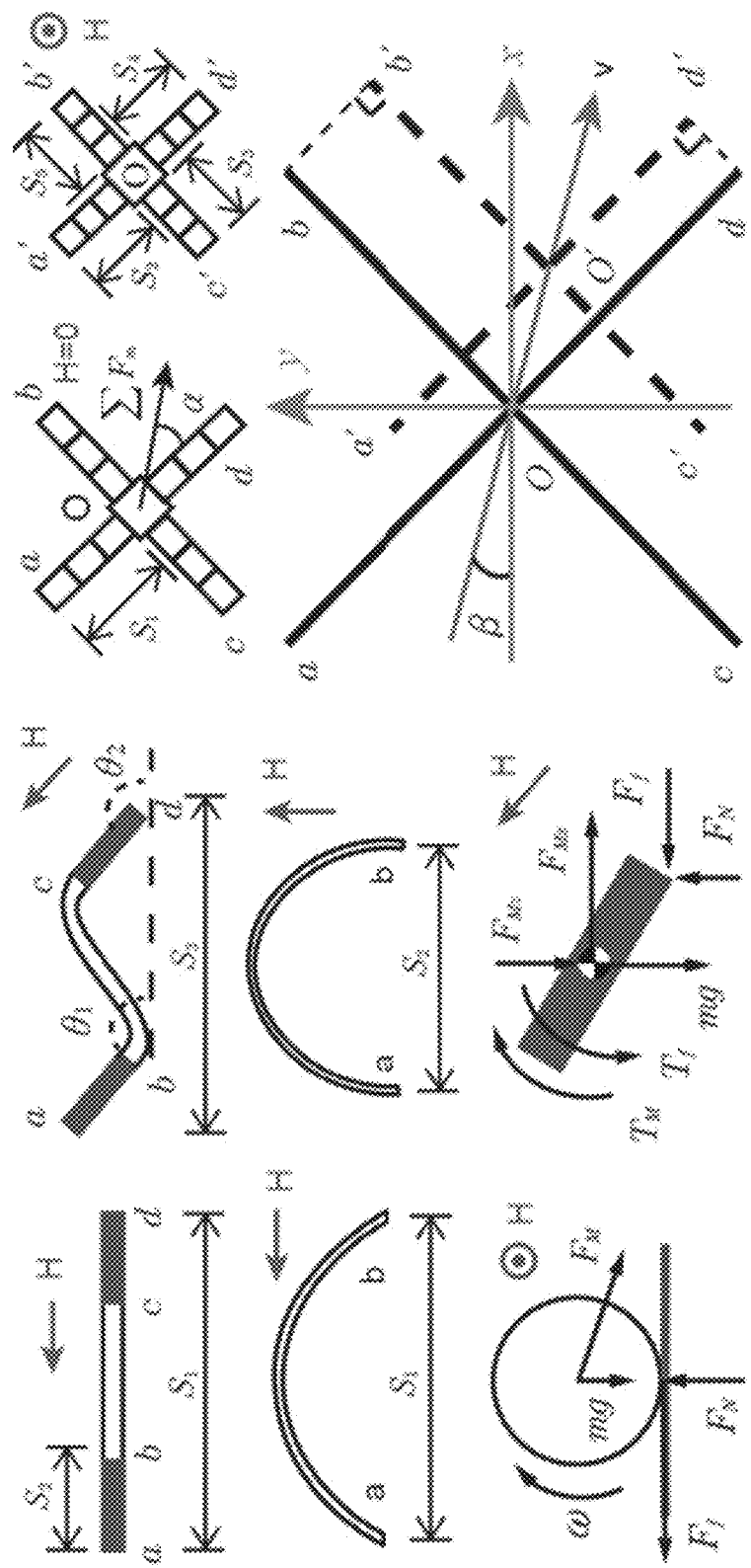

The roboticization of inanimate objects is realized by the directional magnetization of M-skin and the controllable actuation magnetic field. For an inanimate object with a soft or deformable structure, an easy magnetization axis of M-skin perpendicularly to the deformation direction was oriented to achieve a repeatable morphological change (FIG. 12A). On the other hand, for a rigid or nondeformable inanimate object, the easy magnetization axis of M-skin was aligned in parallel to its long axis for holistic locomotion, such as slipping, flipping, and rolling (FIG. 12B). Theoretically, given a constructed M-skin millirobot with an arbitrary structure, it can be modeled as M parts and N contact lines (or points) with the ground. When the magnetic field is applied or removed away, the motion of the ith single anchor is reliable if the criterion meets:

$$F_{fi} + {}_i^{i+1}F_x - {}_i^{i-1}F_x + {}_i^{i-2}F_z + m_i g - {}_i^{i-1}F_z - F_{Nh} - F_{zi} = m, a \neq 0;$$

or $$T_{yi} + {}_i^{i-1}T_y - {}_i^{i+1}T_y - (\mu \sin \theta_i - \cos \theta_i) F_{Nh} r_i = J\ddot{\theta}_i \neq 0,$$

where $r_i$ (i=1, ..., M) is the distance between contact line $c_n$ and mass center $m_i$ of the $i_{th}$ part of robot, $\mu$ is friction coefficient, $\theta_i$ is the angle between line $c_n$-$m_i$ and horizontal direction, $F_{Ni1}$, $F_{fi2}$ are supporting force and friction force from the ground, and $T_{yi}$, $F_{xi}$, $F_{zi}$ are magnetic moment and pulling forces along Y axis, X axis, Z axis, respectively. ${}_i^{i-1}T_y$, ${}_i^{i-1}F_z$, ${}_i^{i-1}F_z$ are explaining equivalent moment to $m_i$ and forces exerted by $m_{i-1}$ part, and ${}_i^{i+1}T_y$, ${}_i^{i+1}F_x$, ${}_i^{i+1}F_z$ are equivalent moment to $m_i$ and forces exerted by $m_{i+1}$ part, respectively (FIG. 3A). In other words, when existing at least one value i that satisfies the above criterions, the designed parasitic millirobot will respond to the magnetic field, i.e., $a_i \neq 0$ indicates translation and $\ddot{\theta}_i \neq 0$ indicates swing or rotation.

Figure 3B:
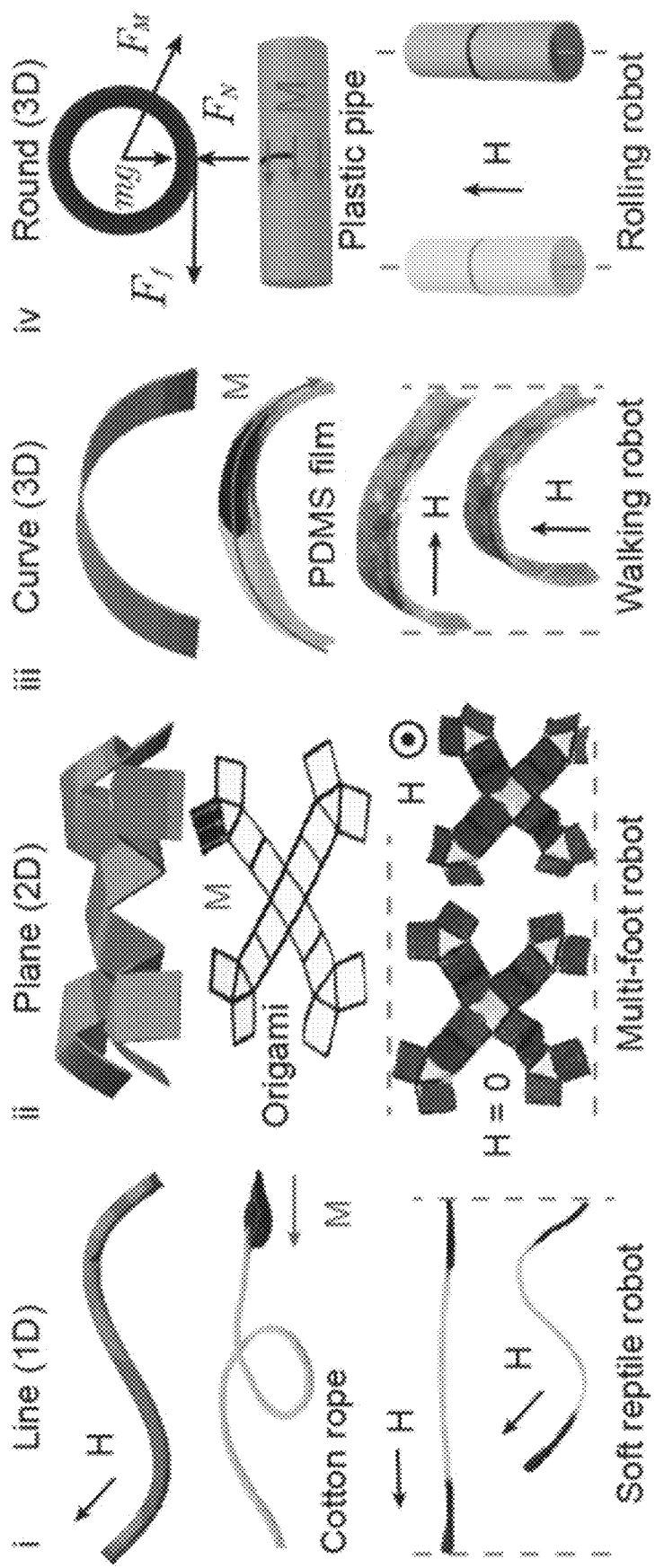
FIG. 3B schematically depicts diverse millirobots from inanimate objects by M-spray coating of the present invention with negligible size variant, including soft cotton rope (line), origami (plane), PDMS film (curve), and plastic pipe (round). mg is the gravity, and FN, Ff, FM are the supporting force, friction force, and magnetic force, respectively.
Figure 3C:
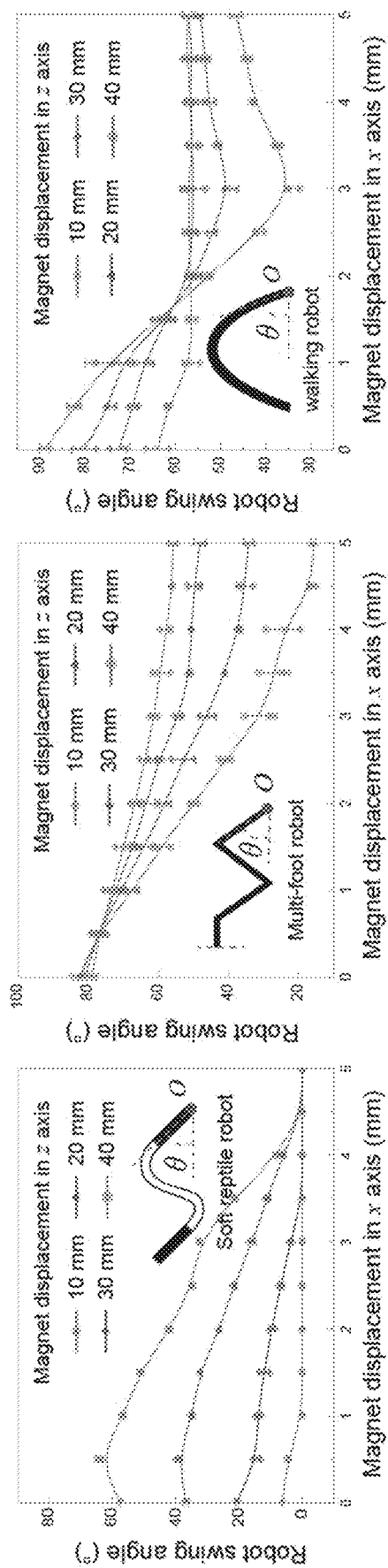
FIG. 3C shows three comparison curves that the deformation and the locomotion of M-skin millirobots are regulated by the strength and the direction of magnetic field and the substrate's material property and inherent structure; error bars indicate the SD for n=3.
Figure 14A:
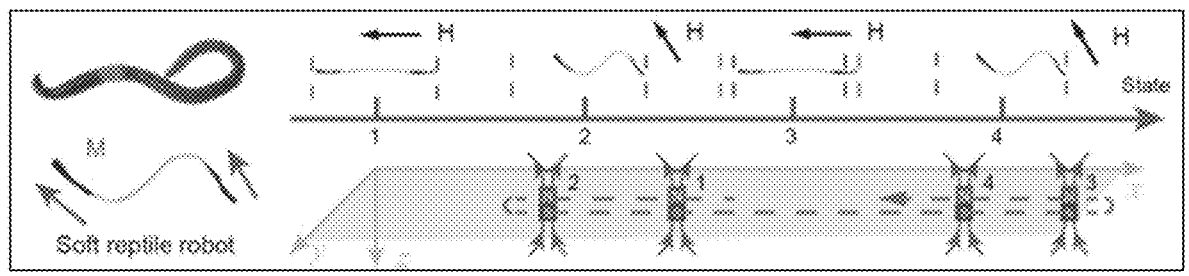
FIG. 14A, FIG. 14B, FIG. 14C, and FIG. 14D show the actuation of M-skin millirobots by permanent magnet.
Figure 14B:
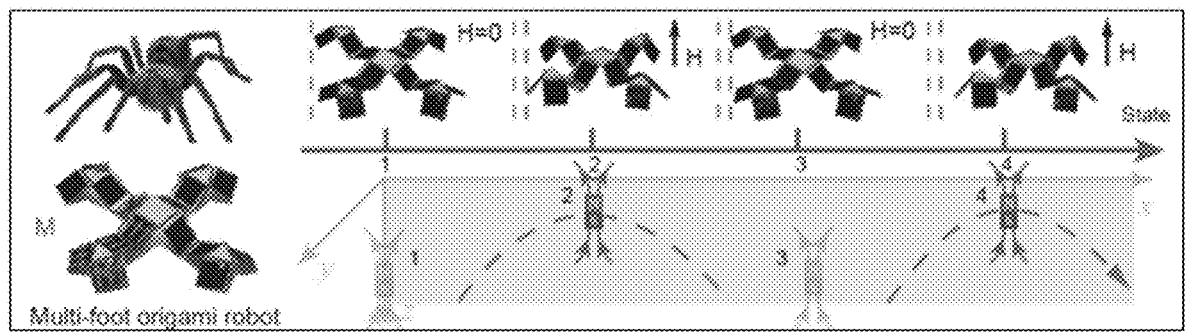
Figure 14C:
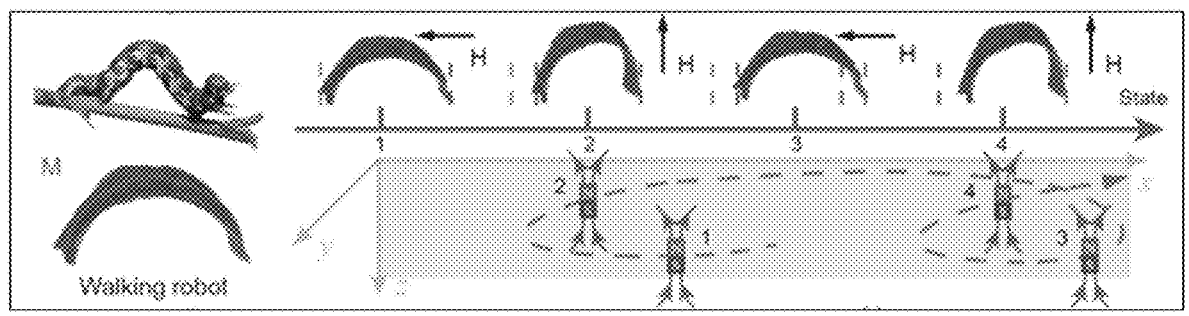
Figure 14D:
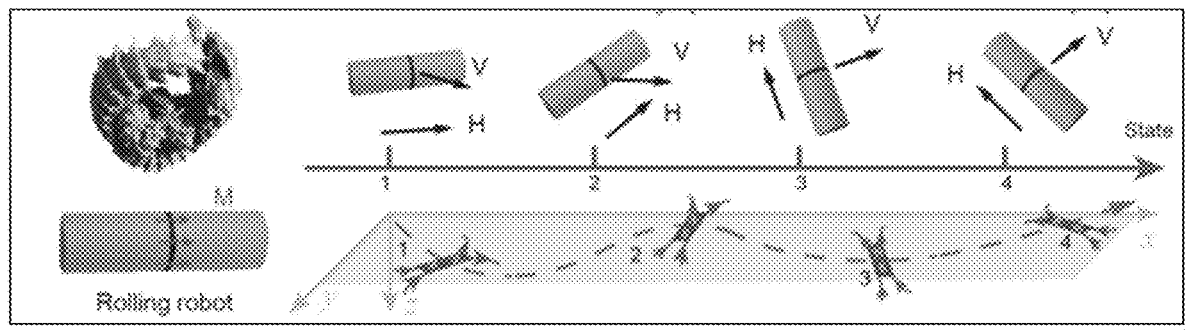
Figure 15A:
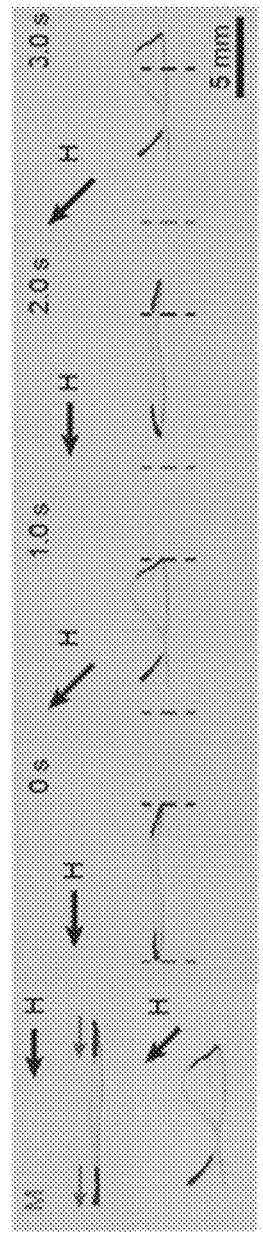
FIG. 15A, FIG. 15B, FIG. 15C, and FIG. 15D show locomotion demonstration of the constructed M-skin millirobots.
Figure 15B:
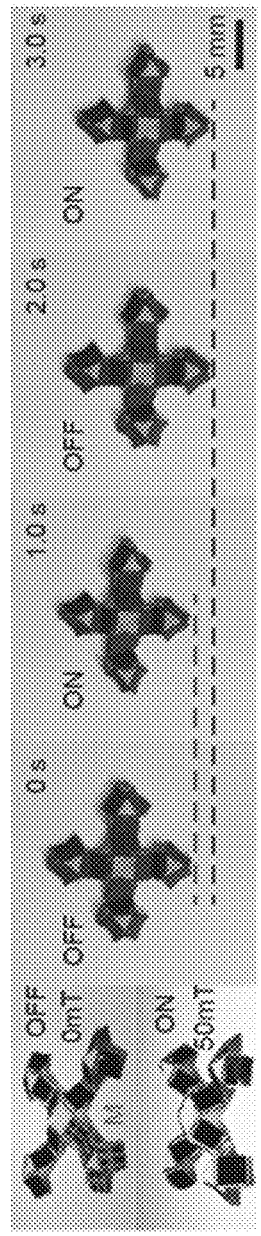
Figure 15C:
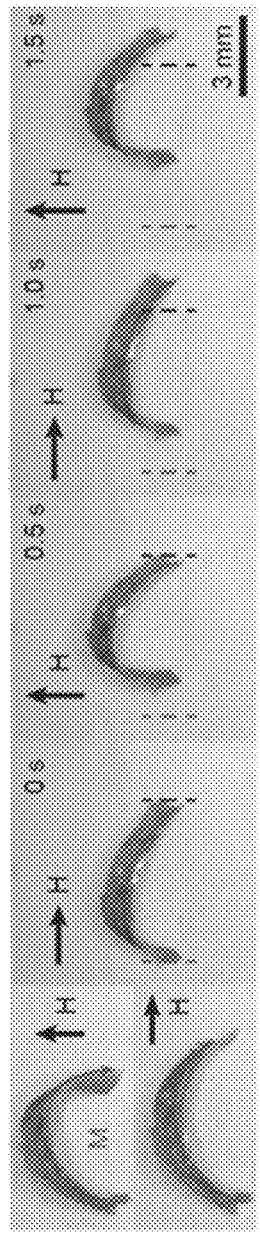
Figure 15D:
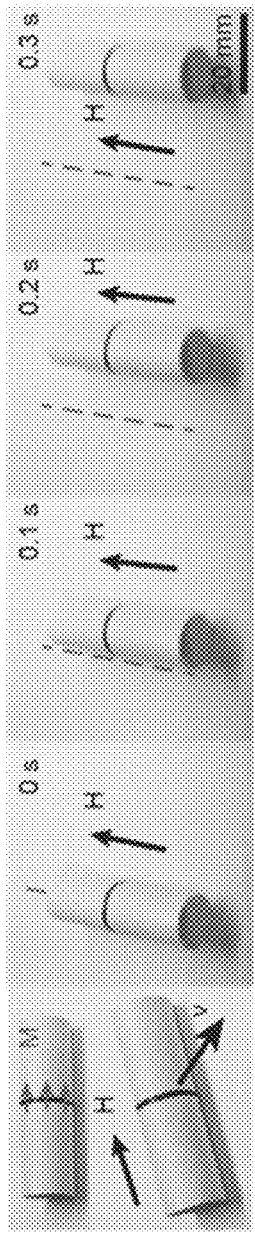
Figure 16E:
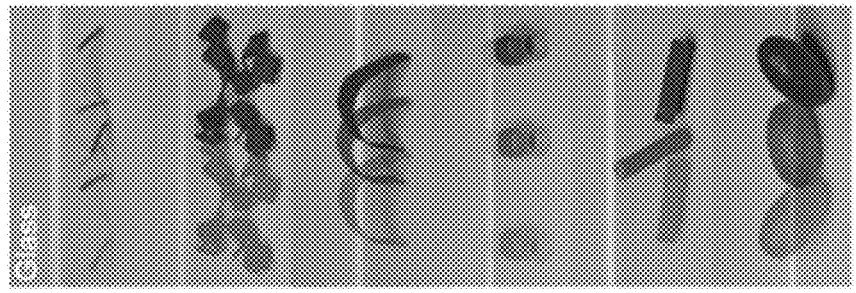
FIG. 16A, FIG. 16B, FIG. 16C, FIG. 16D, and FIG. 16E show the performance evaluation of different motion modes on diverse surfaces.
Figure 16D:
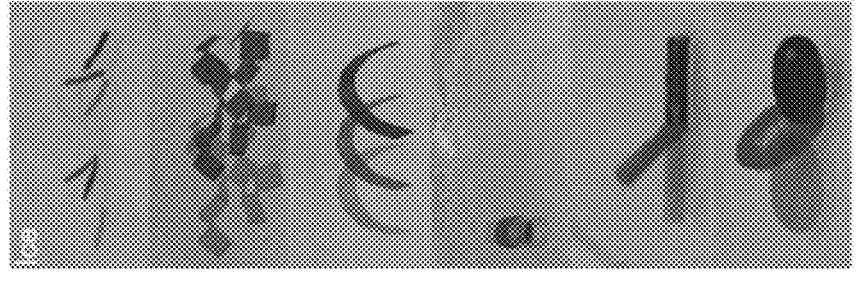
Figure 16C:
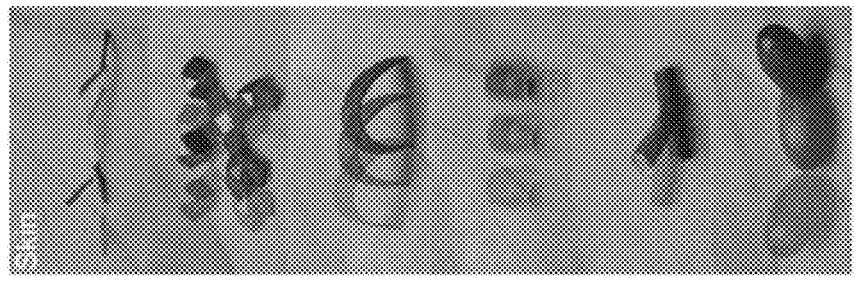
Figure 16B:
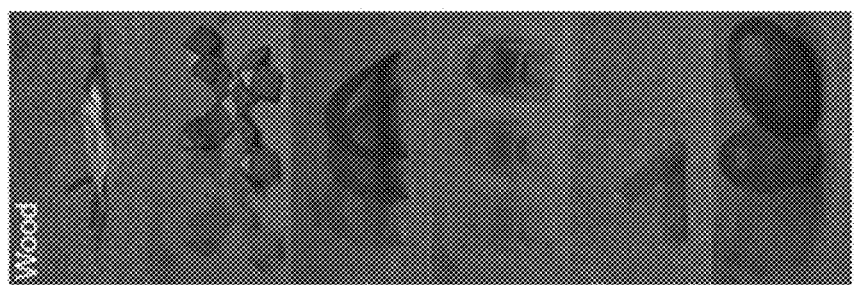
Figure 16A:
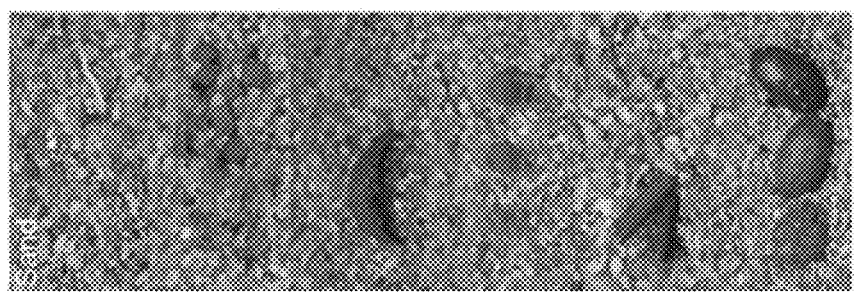
Figure 17:
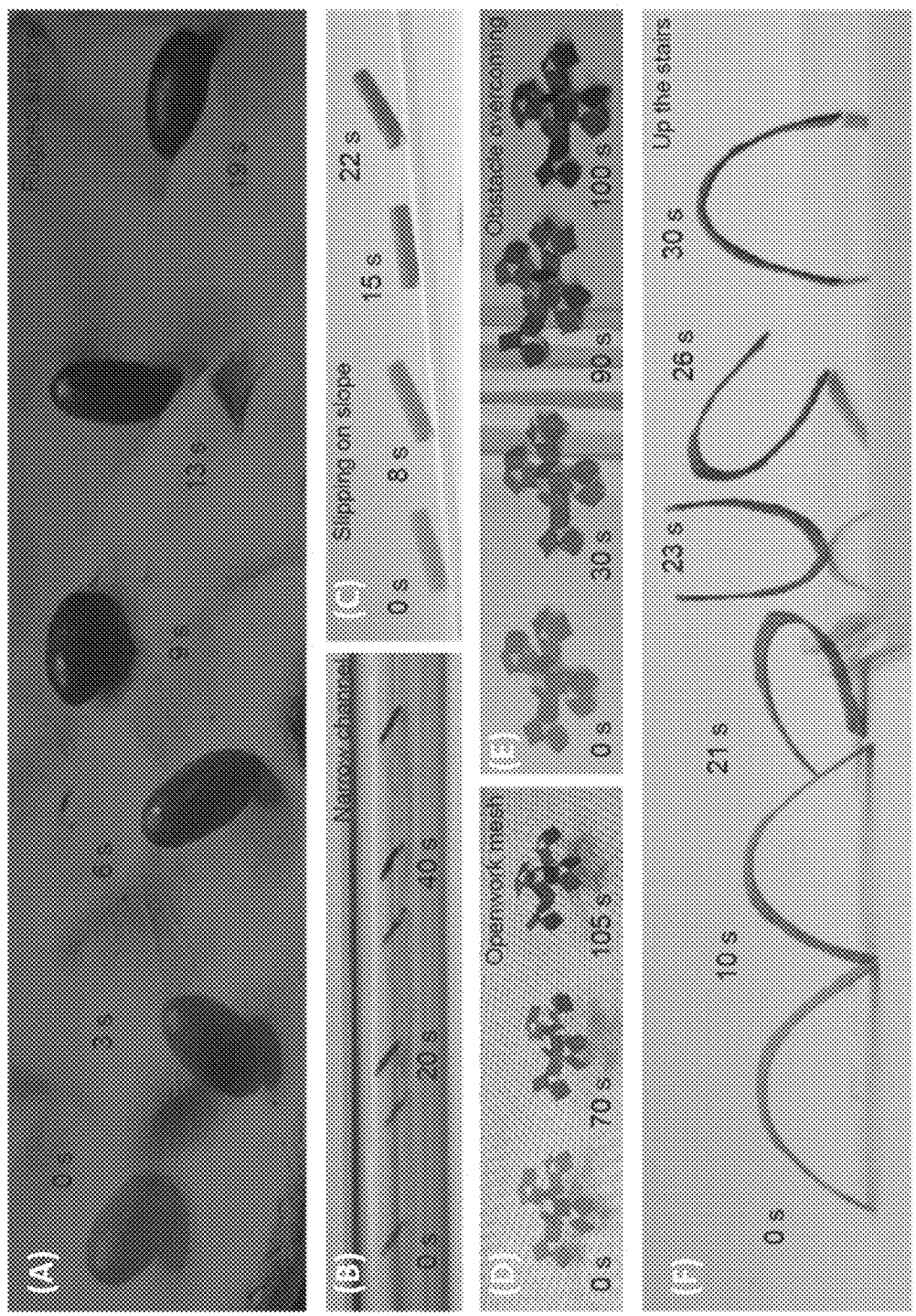
FIG. 17 with labels (A), (B), (C), (D), (E), (F) shows the environment adaptability and obstacle overcoming ability of diverse M-skin millirobots.

To explain the above model and exhibit the versatility of M-spray in turning diverse objects into millirobots, FIG. 3B depicts the process of converting cotton rope (line), origami (flat), PDMS (curve), and plastic pipe (round) into soft reptile robot, multiple-joint robot, walking robot, and rolling robot, respectively (26, 27). The fabrication of these millirobots follows the similar coating, magnetization, and curing process as the M-skin, except for peeling off. Specifically, for the robot with more than one coating area, such as the multi-foot origami robot, a mask is used to protect the unselected region and guarantee accuracy. The detailed fabrication process of these robots is given in Materials and Methods and illustrated in FIG. 13A, FIG. 13B, FIG. 13C, and FIG. 13D3. The actuation of these millirobots is realized by a portable permanent magnet (50 mm by 50 mm by 25 mm) underneath (40 mm), which could generate a magnetic field with a strength of ~50 mT and a gradient of ~1000 mT/m. For the deformable soft reptile robot, the applied swing magnetic field is generated by the reciprocating motion of permanent magnet in the xy plane. With the cooperation of the magnetic pulling force, the constructed reptile robot can creep forward by sliding its two con-tact points alternately (FIG. 14A and FIG. 15A). For the multi-foot origami robot, the permanent magnet moves up and down in the xz plane to achieve curling and stretching of the robot; by repeating, the robot can crawl like a multi-foot insect (FIG. 14B and FIG. 15B). For the walking robot, the permanent magnet moves in the xz plane with an O trajectory, moving the robot forward in an inchworm-like locomotion style (FIG. 14C and FIG. 15C). For the nondeformable plastic pipe, the magnetic force provides the power for rolling, and the magnetic torque steers the rolling direction (FIG. 14D and FIG. 15D). These results indicate that diverse millirobots can be constructed with different attributes just by following the similar standardized M-spray adhesion process, offering an effective on-demand millirobot construction strategy to fulfill tasks with different environments, surface conditions, and obstacles. More detailed locomotion demonstration, modeling, and analysis of each millirobot are given in Supplementary Text (FIG. 16A, FIG. 16B, FIG. 16C, FIG. 16D, and FIG. 16E; FIG. 17 with labels (A), (B), (C), (D), (E), (F); and table 2).

TABLE 2

The performance evaluation summary of different motion modes under diverse surface conditions:

| | Motion performance evaluation | | | | |
|---|---|---|---|---|---|
| Locomotion mode | Glass | Ice | Skin | Wood | Sand |
| Reptile crawling | Medium | Medium | Good | Medium | Medium |
| Multi-foot crawling | Medium | Medium | Good | Good | Good |
| Curved-film walking | Good | Good | Medium | Medium | Poor |
| Pipe rolling | Medium | Poor | Good | Good | Good |
| Stick slipping | Medium | Medium | Medium | Poor | Poor |
| Capsule flipping | Medium | Medium | Good | Good | Good |

The strategy of turning inanimate objects into M-skin millirobots fully uses the structure of the objects, leading to several advantages in adaptivity, miniaturization, and efficiency. As the comparison curves show in FIG. 3C, the deformation and locomotion of M-skin millirobot are regulated by the strength and direction of magnetic field, the objects' material property, and inherent structure. Due to the efficient utilization of the target structure, an inanimate target can be actuated by using a small amount of M-spray with a negligible size increment to the object, which can be as low as 1 per mil in volume. Moreover, because most of the applied magnetic energy contributes to the actuation of the target and very little energy is needed to maintain the M-skin itself, the proposed M-spray has an ultrahigh transportation ability of up to several hundred times its own weight. For instance, 0.01 g of M-spray (after curing) can drive a bulk plastic tube with a weight of 3.63 g under normal-level magnetic field (strength, ~50 mT and gradient, ~1000 mT/m), which is ~360 times its own weight and ~1600 times its own volume. The advantages of M-skin millirobot in high adaptability, negligible size variation, and high working efficiency offer a unique strategy for robot-object interaction at small scales, especially for tasks with limited space.

Figure 4A:
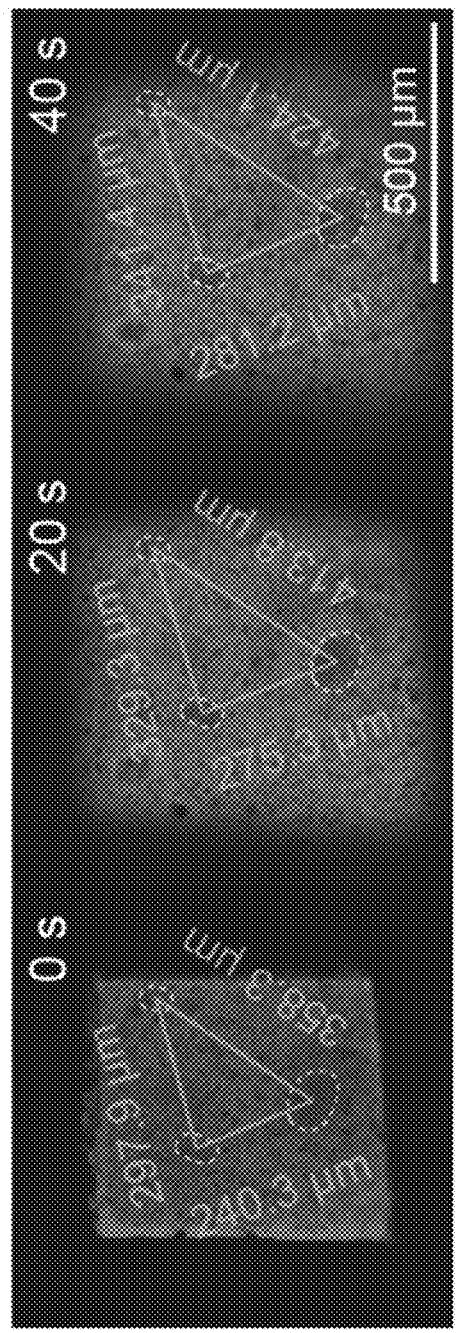
FIG. 4A shows a series of fluorescent photos for the swelling of the present M-skin under wetting.
Figure 4B:
FIG. 4B depicts the reprogramming of cured M-skin's easy magnetization axis from horizontal to vertical under wetting and a 200-mT magnetic field, during which the demonstrated sample with a MP content of 1% shows the reorganization process.
Figure 4D:
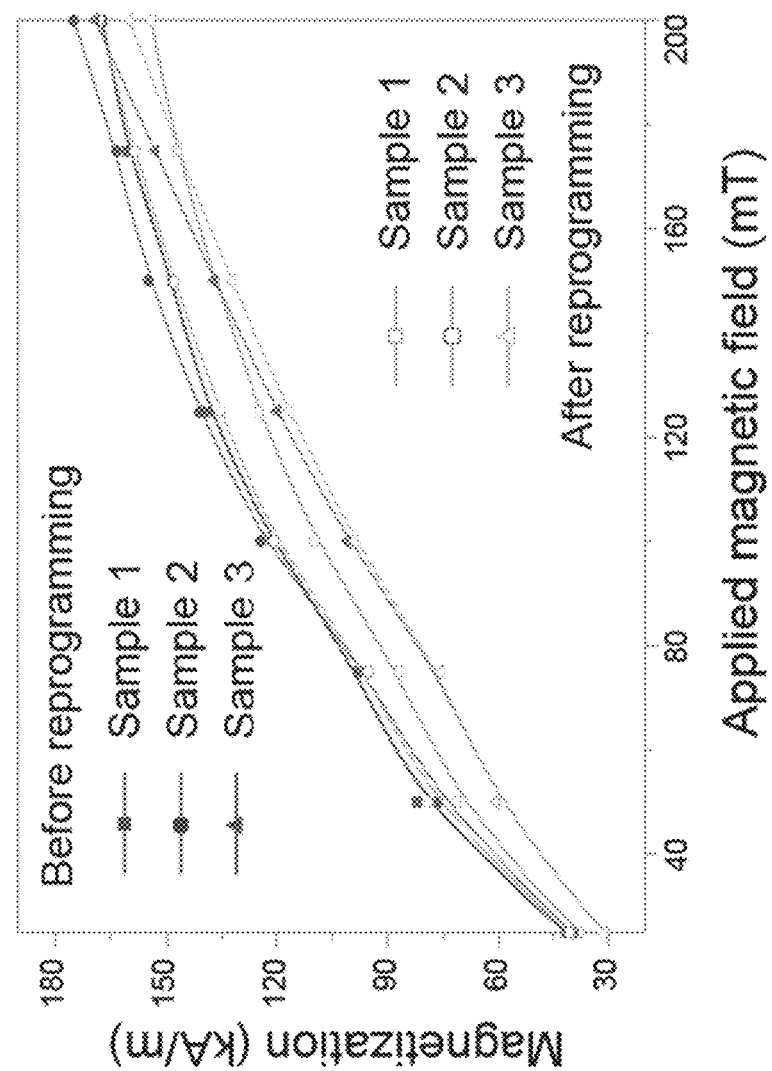
FIG. 4D schematically depicts the quantitative magnetization measurement of M-skin before and after reprogramming, where the tested sample with a MP content of 40% and a size of 5 mm by 5 mm was reprogrammed under 200 mT within 10 min.
Figure 4C:
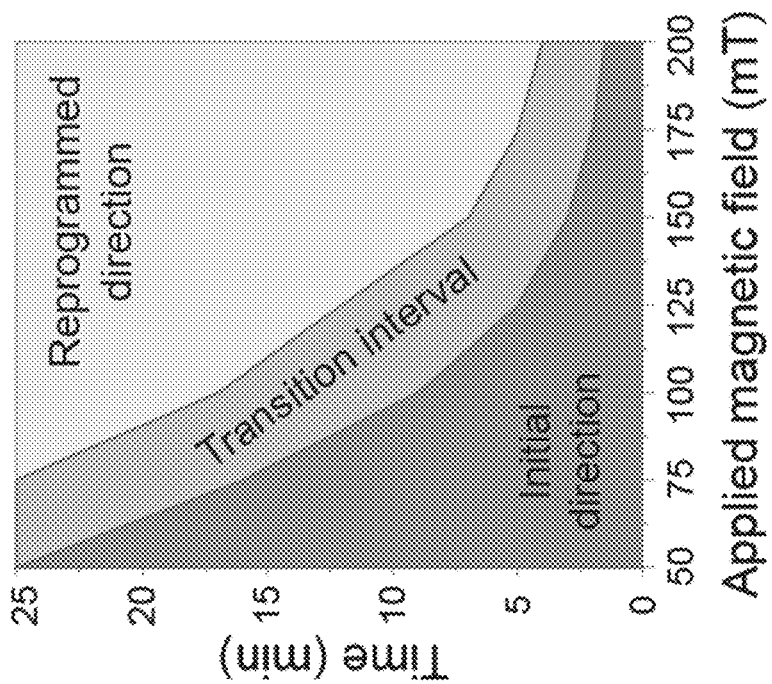
FIG. 4C shows the direction changing state of easy magnetization axis and the corresponding applied magnetic field and reprogramming time according to an embodiment of the present invention.
Figure 18A:
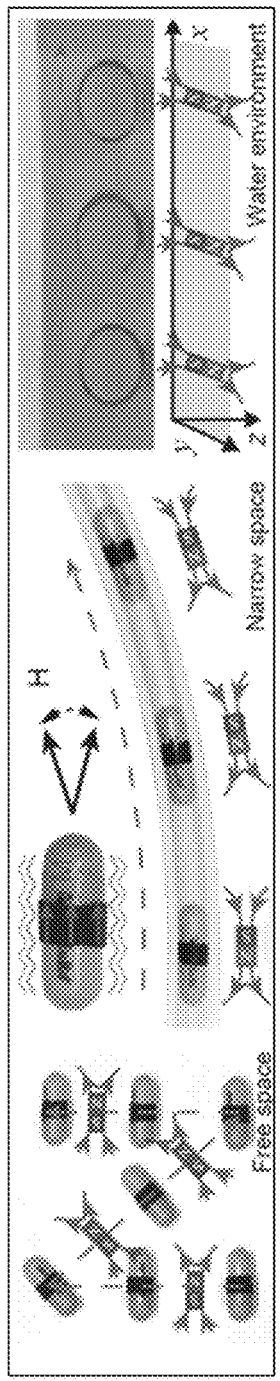
FIG. 18A, FIG. 18B, and FIG. 18C show the constructed M-skin millirobots work in both land and liquid environment.
Figure 18B:
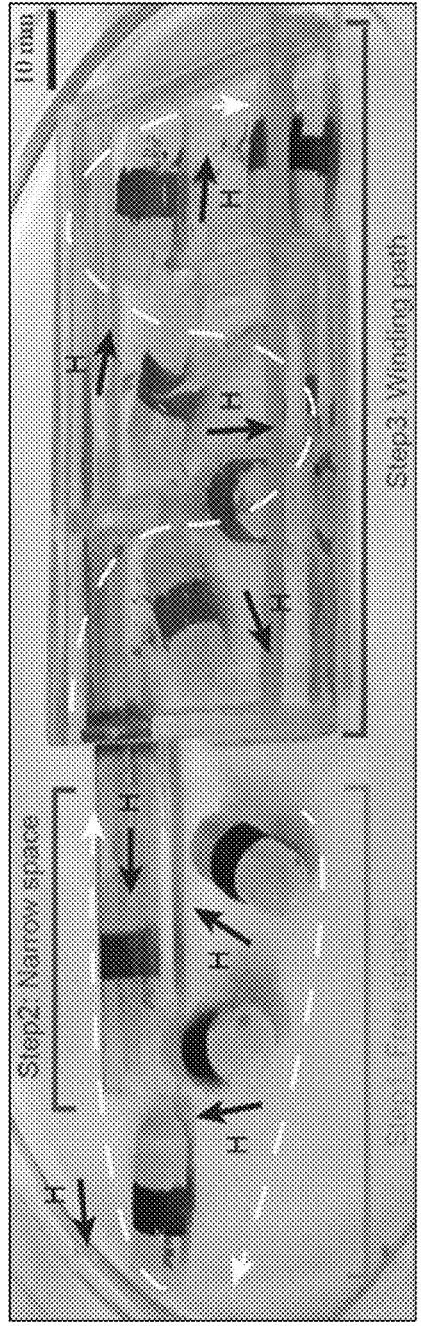
Figure 18C:
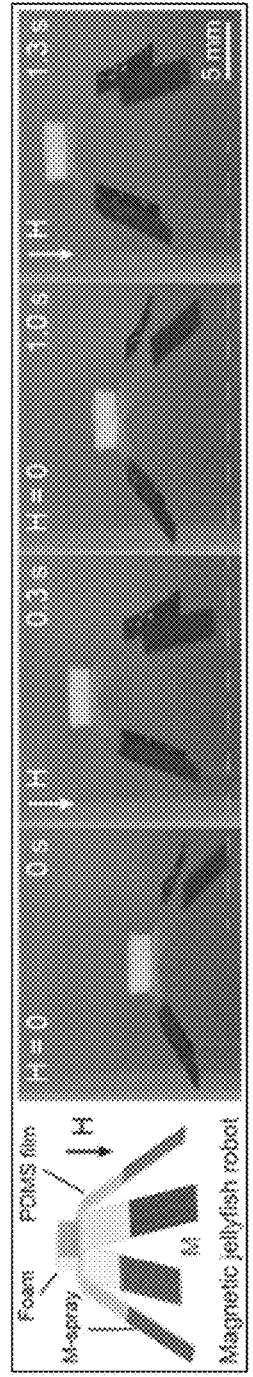

In practice, the reprogramming of the easy magnetization axis in the M-skin with 40% MP mass friction can always be ensured in 5 min as long as the magnetic field strength is sufficient, i.e., larger than 200 mT, based on our experiment trials (FIG. 4C). The results also indicate that the reprogramming efficiency is positively proportional to the applied magnetic field strength. For instance, it takes ~5 min to reprogram the direction of easy magnetization axis from horizontal to vertical under a 200-mT magnetic field, and this process is extended to ~17 min under a 100-mT magnetic field. Note that the magnetic field for actuation (~50 mT) is much lower than the strength for easy magnetization axis reprogramming (200 mT); thereby, FIG. 18A, FIGS. 18B, and 18C show the constructed M-skin millirobots work in both land and liquid environment, in which the robot constructed by M-skin can keep stable and locomote effectively at the wet or liquid environment, as evidenced by the jellyfish robot in FIG. 18C. To quantitatively evaluate the efficiency and stability of the easy magnetization axis after realignment, contrast tests were performed to measure the magnetization of M-skin before and after reprogramming. As shown in FIG. 4D, after reprogramming under a 200-mT magnetic field for 10 min, the magnetization of all the three M-skins exhibited a small discrepancy (13.0, 6.8, and 9.2 kA/m under 200 mT) compared with their initial states, i.e., discrepancy of 7.7, 3.9, and 5.4% for samples 1, 2, and 3, respectively. These results suggest that the proposed reprogramming strategy is feasible and repeatable for rearranging the easy magnetization axis of M-skin.

Figure 4E:
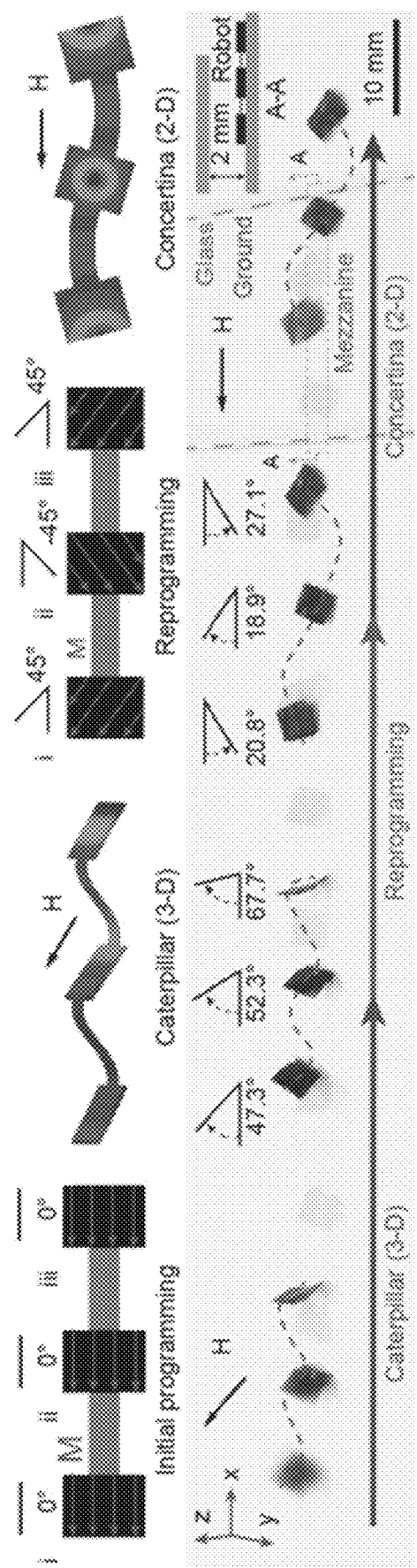
FIG. 4E shows the three-section reptile robot demonstrates caterpillar (3D) and concertina (2D) motion before and after reprogramming without structure changing.
Figure 4F:
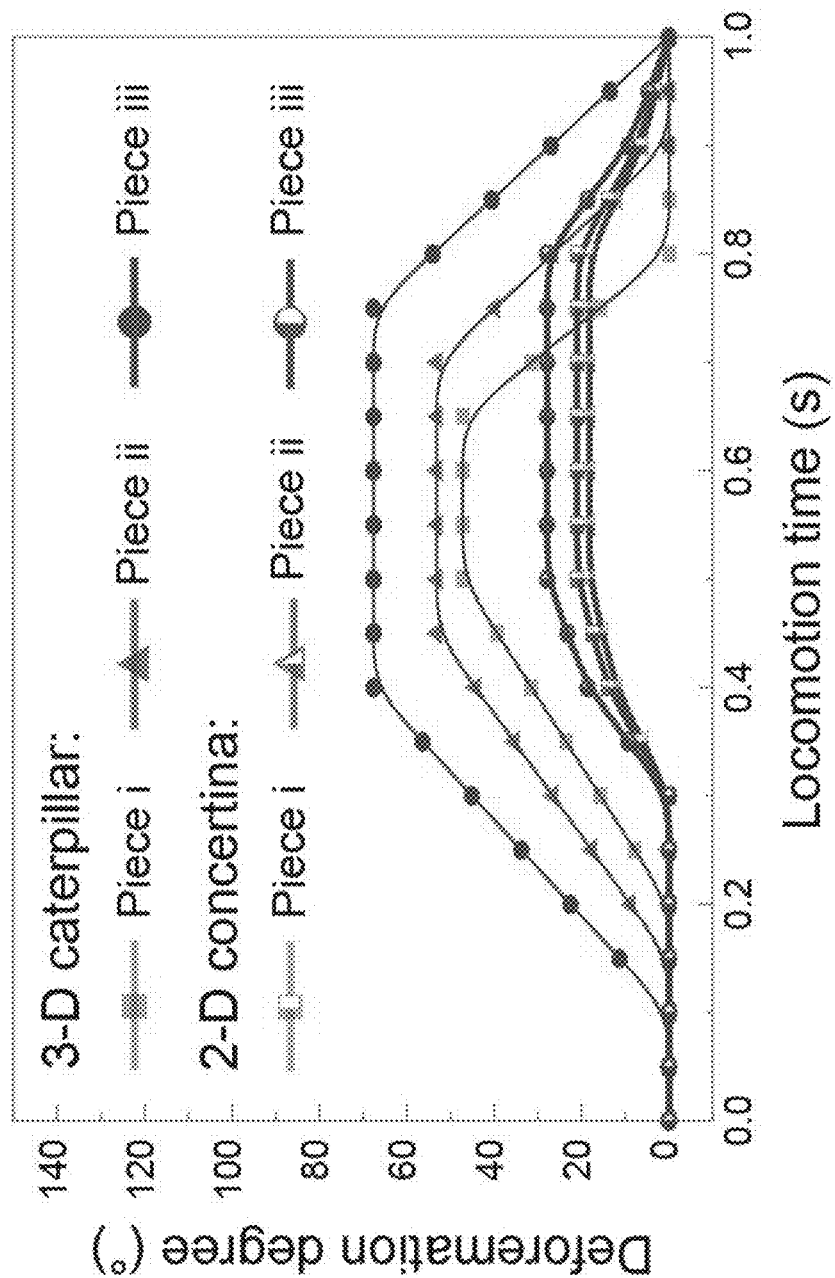
FIG. 4F shows the deformation of robot during 3D caterpillar and 2D concertina motion, respectively.
Figure 4G:
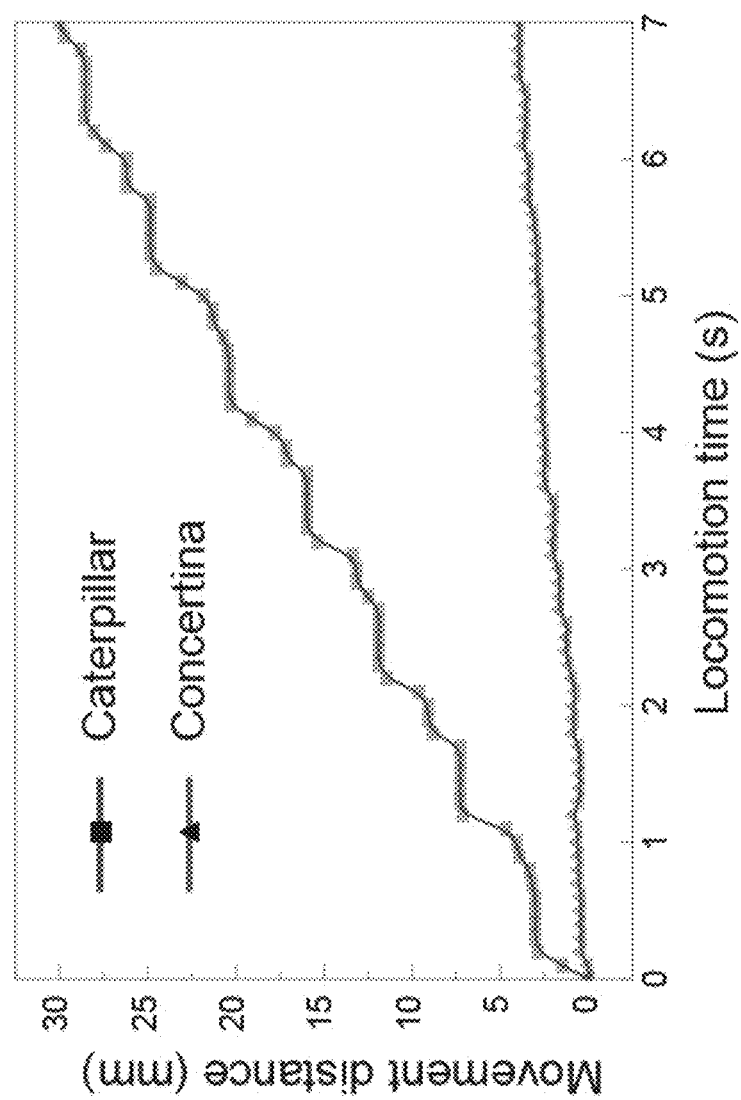
FIG. 4G shows the step size comparison between caterpillar (3D) and concertina (2D) motion under the same magnetic field strength with a frequency of 1 Hz.
Figure 4H:
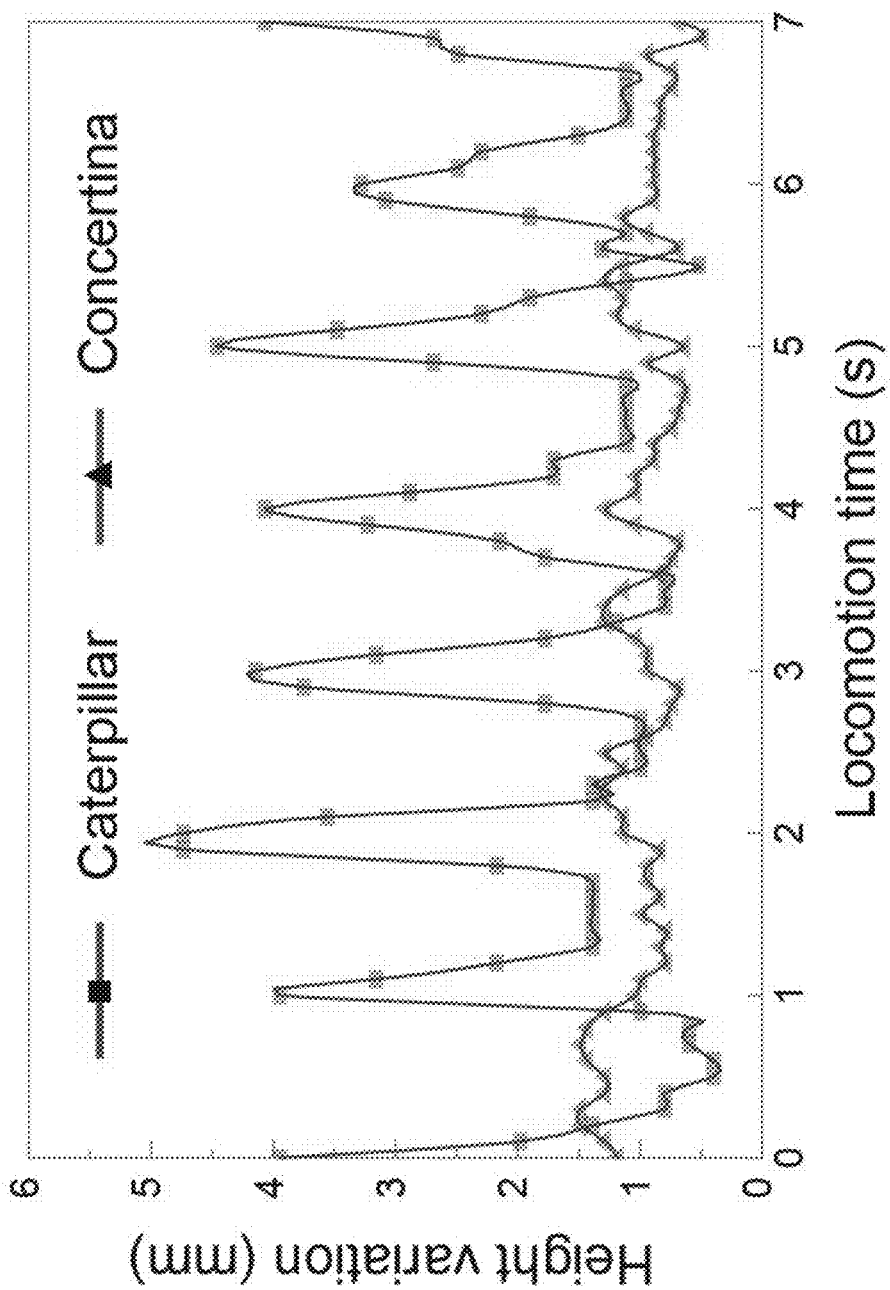
FIG. 4H shows robot height variation as time changes during caterpillar (3D) and concertina (2D) motion.

The on-demand reprogramming ability endows an M-skin millirobot with high adaptivity to achieve diverse locomotion. To demonstrate this, a simple reptile millirobot (28) was constructed by coating M-spray on three sections of a plastic belt (FIG. 4E). Initially, the easy magnetization axes of these three M-skins are aligned along the horizontal. When a swing magnetic field is applied, the M-skins will tilt up or down, and the robot crawls forward by alternating the front anchor and rear anchor like a caterpillar. On the other hand, after the easy magnetization axes are reprogrammed along the diagonal, the millirobot can shrink to an "S" form under a horizontal magnetic field and restore when removing the magnetic field. By repeatedly applying and withdrawing the magnetic field, the millirobot deforms like a concertina to move forward by alternating anchors. Further quantitative analyses reveal that the millirobot with the same structure can exhibit essentially different locomotion styles in deformation angle (FIG. 4F), step size (FIG. 4G), and height variation (FIG. 4H) by reprogramming. Benefiting from the on-demand reprogramming ability, the M-skin millirobot can switch its motion between 3D caterpillar and 2D concertina to adapt to different environments, such as moving with a high speed by cater-pillar motion (~10-fold faster than concertina motion) at free space and clinging to the ground by concertina motion for crossing a narrow crevice (interval, ~2 mm) (FIG. 4E). More details about the locomotion analysis can be found in Supplementary Text.

Magnetic-Induced Disintegration

Figure 5A:
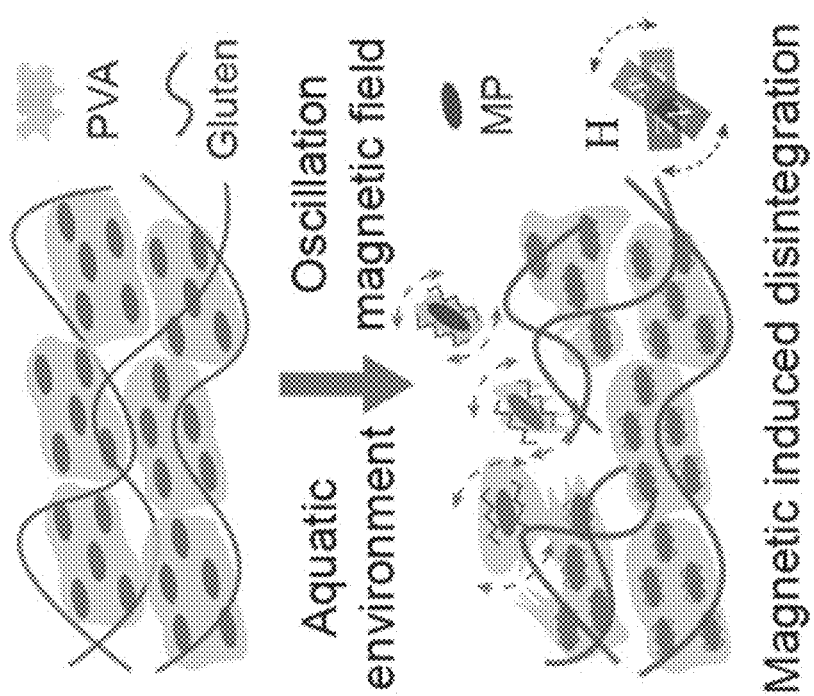
FIG. 5A schematically depicts the oscillation magnetic-induced disintegration of M-skin in aquatic environment.
Figure 5C:
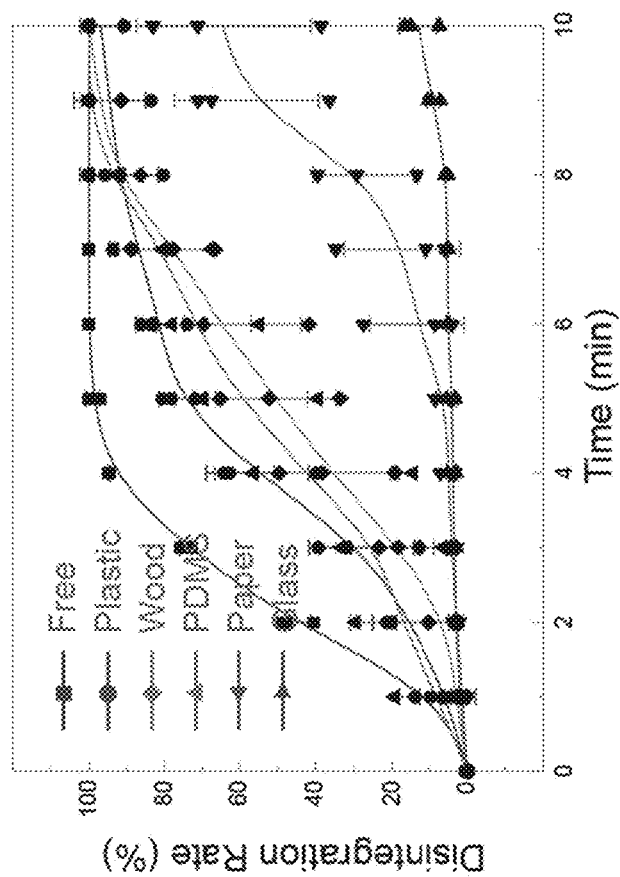
FIG. 5C shows M-skin disintegration rate over time on different materials' surfaces under the oscillating magnetic field with a strength of 10 mT and a frequency of 1 Hz; error bars indicate the SD for n=3.
Figure 5B:
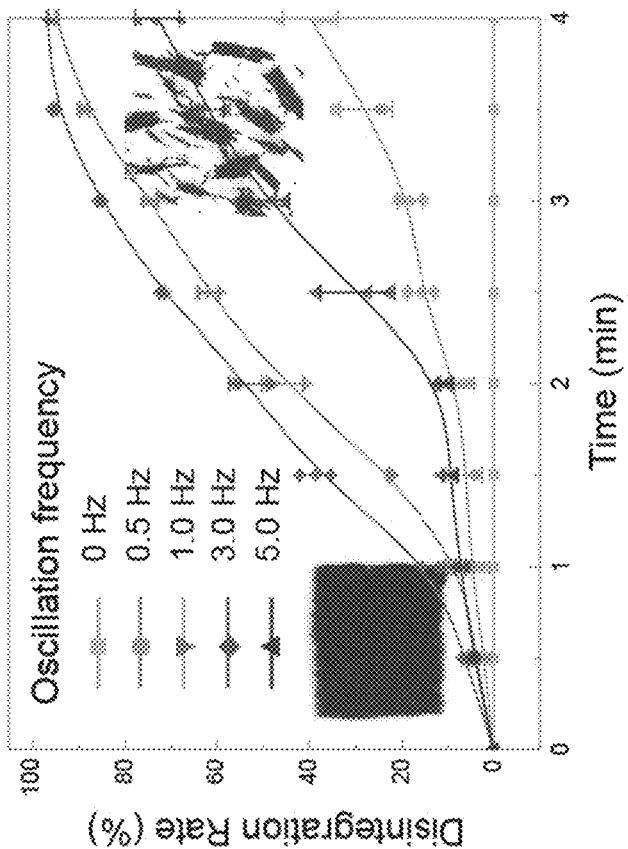
FIG. 5B shows free M-skin disintegration rate over time, where the size of cured M-skin is 5 mm by 5 mm under a 10-mT oscillating magnetic field with a frequency from 0 to 5 Hz; error bars indicate the SD for n=3.
Figure 5D:
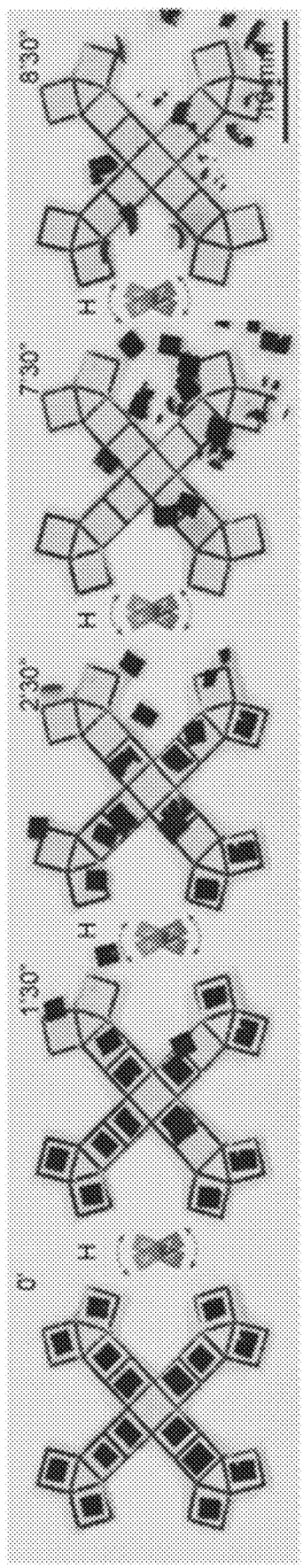
FIG. 5D is a series of photographs depicting the shedding and disintegration process of M-skin from a multi-foot origami robot.
Figure 19B:
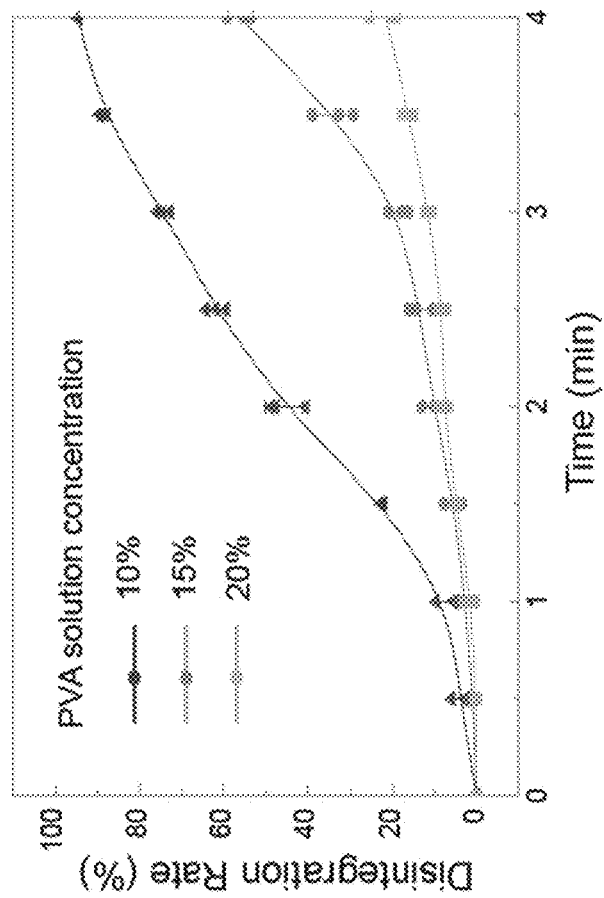
FIG. 19A and FIG. 19B show the controllable magnetic-induced disintegration of M-skin in aquatic environment.
Figure 19A:
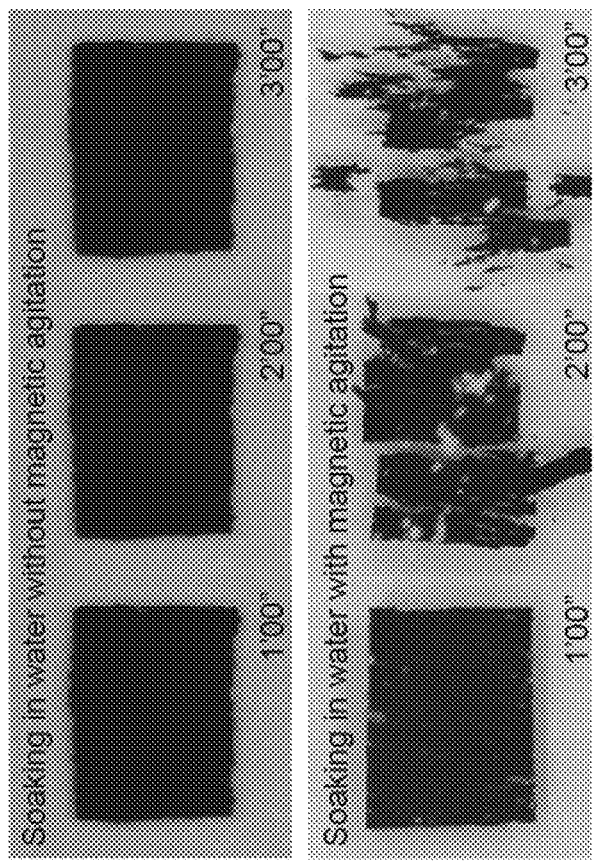
Figure 20A:
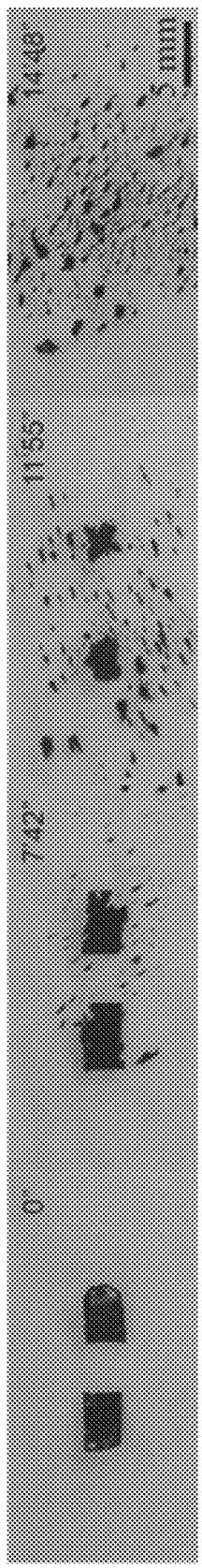
FIG. 20A, FIG. 20B, FIG. 20C depict the process that M-skin detaches after task completing from target inanimate objects.
Figure 20B:
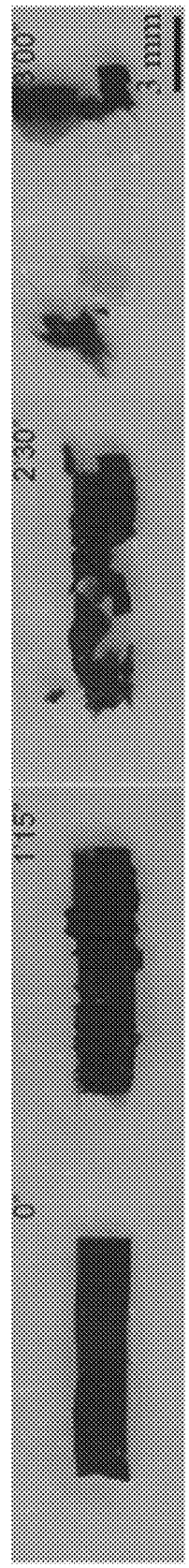
Figure 20C:
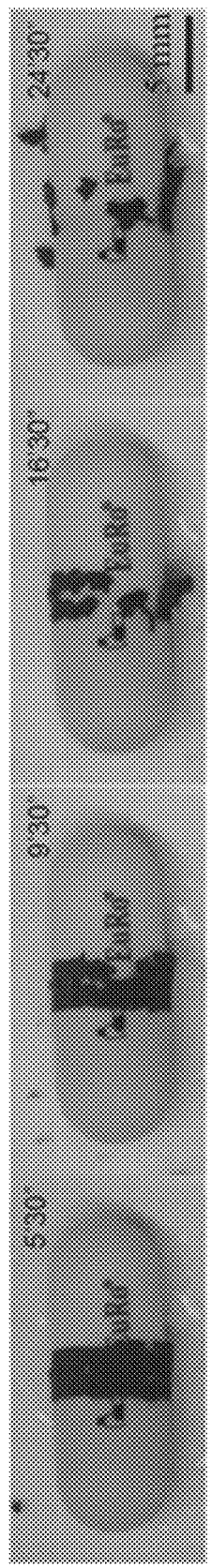

The cured M-skin has good stability in still water or under a static magnetic field due to the low solubility of PVA at normal temperature (FIG. 19A), which means that an M-skin millirobot can remain stable in an aqueous environment. However, it can be controllably disintegrated by increasing the kinetic energy of MPs to overcome the inner constraints via applying an oscillating magnetic field in an aqueous environment (FIG. 5A and FIG. 19A). As shown in FIG. 5B, the disintegrated speed of M-skin is positively proportional to oscillating frequency f from 0 to 3 Hz, and the disintegration can be completed within 4 min under a 10-mT magnetic field with a frequency of 1 Hz. It is noted that the disintegration time will take several-fold longer after M-skin adheres to objects because the joint surface can enhance its structural integrity (FIG. 5C and FIG. 20A, FIG. 20B, FIG. 20C). The optical images in FIG. 5D display the shedding and disintegration of M-skin from the multi-foot origami robot under the aqueous environment, where a 10-mT oscillation magnetic field with a frequency of 1 Hz was applied. Although the existing millirobot provides opportunities for effective cargo transportation, the postprocessing of the robot after task remains a big challenge, which may still cause unpredicted side effects. Magnetic-induced disintegration ensures that the constructed M-skin millirobot can disintegrate on command (FIG. 20A, FIG. 20B, FIG. 20C), making it suitable for controllable cargo unloading. Moreover, the component of MPs is pure Fe in our M-skin design. As a natural metal (ferritin) in the human body, the side effect from its disintegration is negligible (29), making it a good candidate for biomedical applications.

To further understand the disintegration process, the effect of mass fraction and pH value on the disintegration speed was evaluated. Because gluten can enhance the mechanical property of an M-skin and PVA can endow an M-skin with better film-forming ability and adhesiveness, both a lower mass fraction of gluten and a lower concentration of PVA solution will accelerate disintegration (FIG. 5E and FIG. 19B). For instance, an M-skin without gluten can be disintegrated completely under the magnetic oscillation within 2 min, whereas an M-skin with 10% gluten can remain more than half intact after 4 min under disintegration conditions. Similarly, the M-skin adopting a 10% PVA solution concentration can be disintegrated in about 4 min, whereas the one adopting a 20% concentration of PVA solution disintegrated 20% in the same time. However, it is worth noting that the mass fraction of gluten and the concentration of PVA solution should be kept in a proper value when in use, i.e., PVA solution concentration of ~10% and gluten of ~5%, by weighing the fabrication, adhesiveness, actuation, and reliability of M-skin.

Figure 5G:
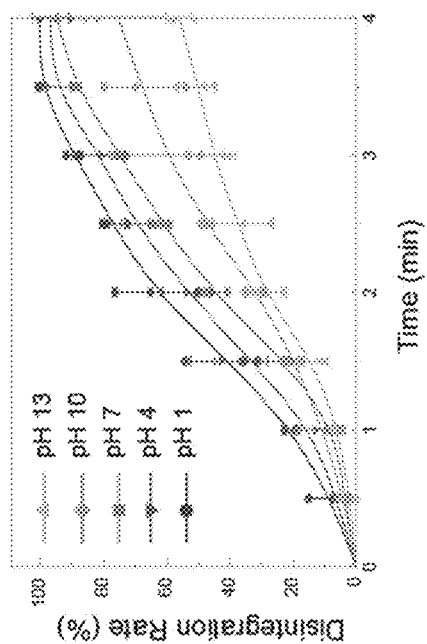
FIG. 5G shows M-skin disintegration rates over time under the same oscillating magnetic field (10 mT, 1 Hz) and diverse environmental pH (from 1 to 13); error bars indicate the SD for n=3.
Figure 5F:
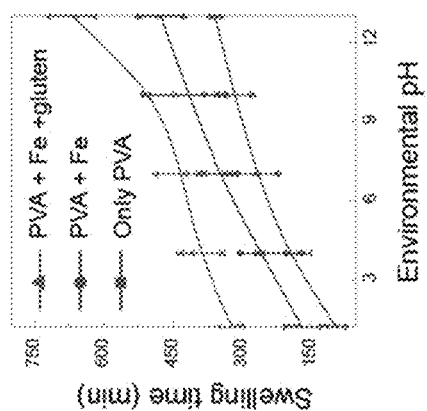
FIG. 5F shows the changes in swelling time of M-skin against the environmental pH changes from 1 to 13; error bars indicate the SD for n=3.
Figure 5E:
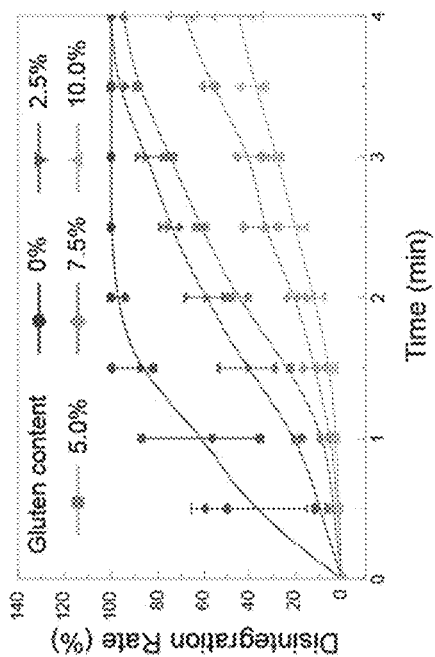
FIG. 5E shows different disintegration rates of M-skin over time when the gluten content changes from 0 to 10%; error bars indicate the SD for n=3.
Figure 21A:
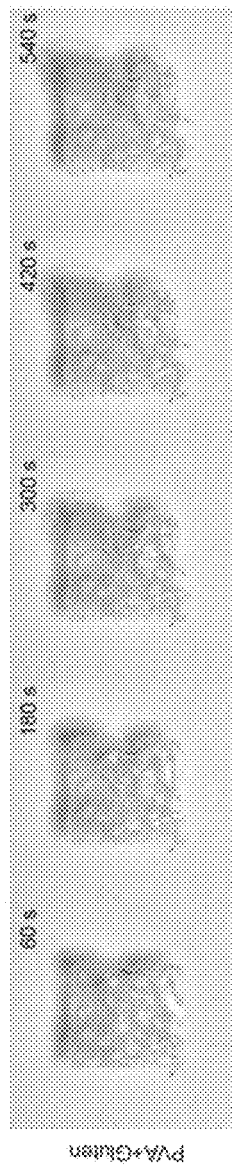
FIG. 21A, FIG. 21B, FIG. 21C, and FIG. 21D the disintegration of M-skin with different material components in strong acid environment (pH 1) without magnetic oscillation.
Figure 21B:
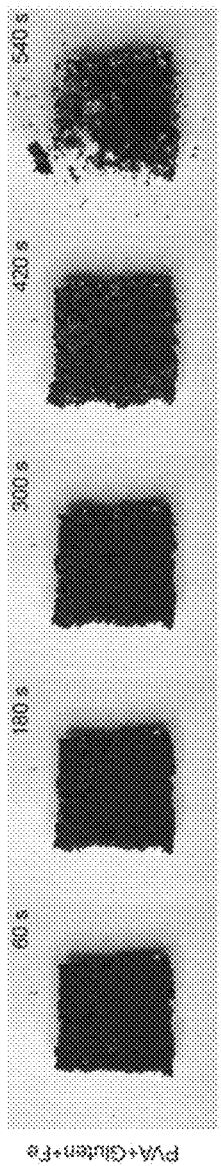
Figure 21C:
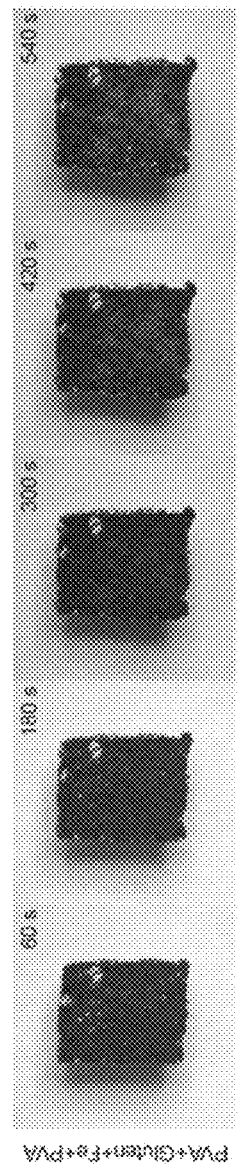
Figure 21D:
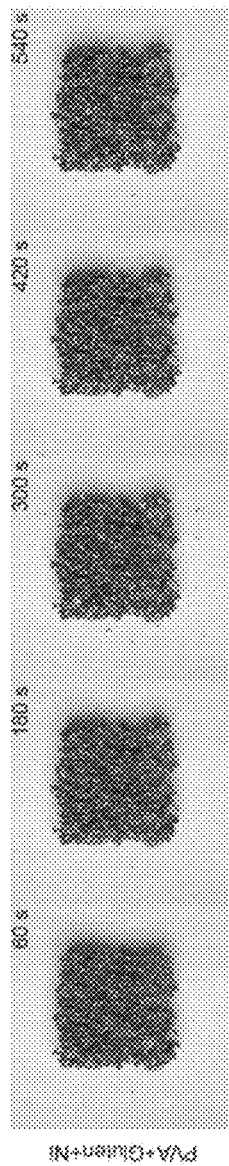

Regarding the effect of pH value, the swelling and disintegrating process of M-skin are accelerated when the acidity is enhanced because the weak hydrogen bonds between PVA chains will be replaced by the strong hydrogen bonds between PVA chains and hydrogen ions (FIGS. 5F and 5G, and tables 3 and 4). Specifically, the M-skin will start to disintegrate in about 8 min under the strong acid environment (pH 1) even without magnetic oscillation, caused by the chemical reaction between iron particles inside the M-skin and the hydrogen ions inside the acid (FIG. 21A and FIG. 21B). To prolong the effective working time of M-skin in the strong acid environment, two kinds of improvements can be adopted: one is to coat an additional PVA layer on the surface of M-skin after curing; the other is to change the MPs into other contents that do not react with the hydrogen ions inside the acid, such as nickel. As shown in FIG. 21C and FIG. 21D, the additional PVA covering can extend the disintegration without magnetic oscillation from ~8 to ~15 min, whereas the M-skin with nickel particles can keep stable in the strong acid environment even after 30 min.

TABLE 3

The swelling and disintegration of M-skin without magnetic oscillation under different environmental temperature and pH:

| Temperature (° C.) | State | Time (s) | | | | |
|---|---|---|---|---|---|---|
| | | pH 1 | pH 4 | pH 7 | pH 10 | pH 13 |
| Room Temperature (20° C.) | Full Swelling | 320 ± 26 | 394 ± 48 | 431 ± 52 | 485 ± 33 | 666 ± 50 |
| | Disintegration | 1480 ± 83 | 4480 ± 703 | 6260 ± 600 | 8700 ± 950 | Never |
| Body Temperature (37° C.) | Full Swelling | 148 ± 18 | 311 ± 31 | 376 ± 36 | 422 ± 36 | 467 ± 43 |
| | Disintegration | 620 ± 91 | 3040 ± 682 | 4820 ± 330 | 6386 ± 388 | 10400 ± 916 |

TABLE 4

The swelling and disintegration time of cured film composed of different materials without magnetic oscillation:

| Material Composition | State | Time (s) | | | | |
|---|---|---|---|---|---|---|
| | | pH 1 | pH 4 | pH 7 | pH 10 | pH 13 |
| PVA Solution | Full Swelling | 168 ± 39 | 256 ± 50 | 350 ± 38 | 416 ± 85 | 477 ± 48 |
| | Disintegration | 3500 ± 641 | 4486 ± 280 | 5386 ± 1120 | 7560 ± 1101 | Never |
| 40% Fe in PVA Solution | Full Swelling | 93 ± 20 | 199 ± 50 | 266 ± 44 | 315 ± 33 | 358 ± 13 |
| | Disintegration | 760 ± 124 | 3040 ± 307 | 4300 ± 283 | 5780 ± 510 | Never |
| 40% Fe and 10% gluten in PVA Solution | Full Swelling | 320 ± 26 | 394 ± 48 | 431 ± 52 | 485 ± 33 | 666 ± 50 |
| | Disintegration | 1480 ± 183 | 4480 ± 703 | 6260 ± 600 | 8700 ± 950 | Never |

M-Skin-Covered Catheter for On-Demand Active Navigating

The catheter is a widely used tool to treat diseases or to perform surgical procedures in the body cavity, duct, or vessel. Because of its thin and flexible structure, the insertion is usually conducted passively, and the corner crossing is very challenging in practice. Here, an M-skin catheter was constructed with active steering and navigating abilities by coating M-spray (thickness, ~150 μm; length, 8 mm) on the existing flexible catheter head end (diameter, 1 mm) followed by an axial magnetization (FIG. 6A). In this design, the M-spray mainly plays two functions: One is to provide the magnetic force F to pull the flexible wire forward, and the other is to steer the course by magnetic torque T. Same as existing magnetic steering catheters (30-32), the bending radius r and degree θ of the tip depend on the ratio of flexible length LFlex and stiff length LStiff, as well as the strength and direction of applied magnetic field. By leveraging an appropriate constraint and magnetic field, the constructed M-skin catheter can perform sharp or smooth turns.

Figure 22A:
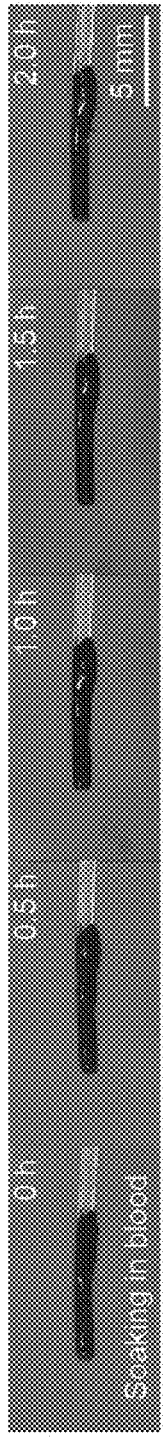
FIG. 22A, FIG. 22B, FIG. 22C, FIG. 22D, FIG. 22E show the influence of physiological blood flow on the locomotion speed and disintegration process of M-skin catheter.
Figure 22C:
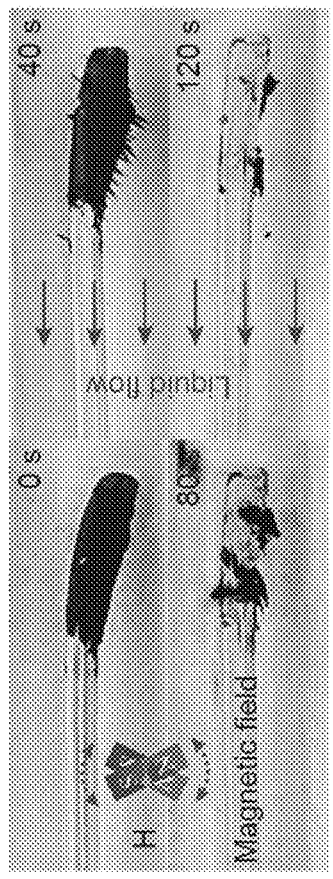
Figure 22B:
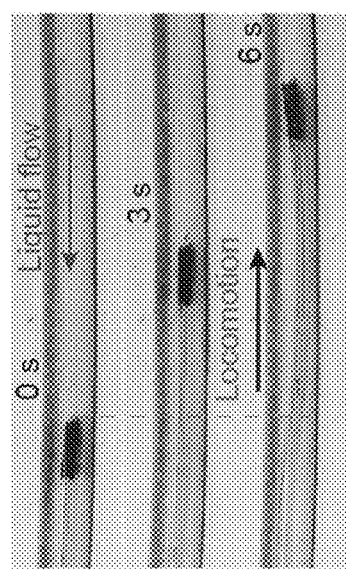
Figure 22E:
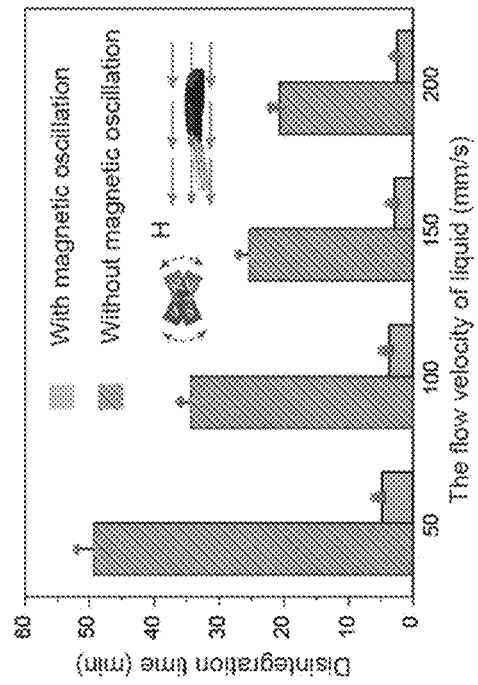
Figure 22D:
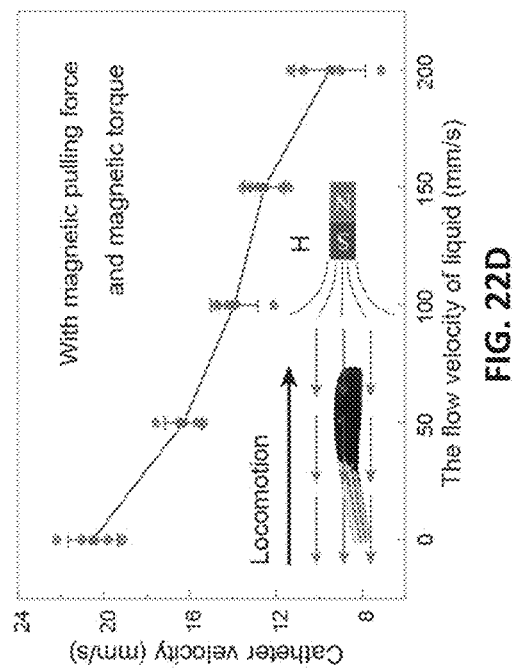

To demonstrate the active guidance ability of the M-skin catheter, the thrombus in a narrow blood vessel model (minimum diameter, 4 mm and maximum diameter, 9 mm) with a 120° branch corner was targeted. As illustrated in FIG. 6B, the con-structed M-skin catheter first moves forward ~45 mm to the fork of blood vessels in 20 s by manual feeding and magnetic pulling. After that, magnetic torque was steered to a direction by rotating 60° clockwise in order to make the catheter turn right about 60° into the target branch. Last, the catheter transports forward ~30 mm in 60 s to approach the target. Considering the blood flow in practical vessels, the motion ability and stability of an M-skin catheter were studied under the effects of liquid flow (FIG. 22A, FIG. 22B, FIG. 22C, FIG. 22D, FIG. 22E). First, the impact of still blood itself on the disintegration is negligible, and the M-skin of the catheter can keep stable even after 2 hours (FIG. 22A). The moving speed of catheter decreased as the liquid flow velocity increased (FIG. 22D), but the influence of the blood flow on locomotion would not be a major issue because manual wire feeding is always used in clinical applications. For disintegration without the oscillating magnetic field, the M-skin was stable for 50 to 20 min as the liquid flow velocity changed from 50 to 200 mm/s (FIG. 22E), which is an acceptable value to meet the requirement of many clinical application cases.

Benefiting from the features of on-demand fabrication and reprogramming, our method can also set more than one coating region to construct the multi-point M-skin catheter flexibly. Different from the conventional magnetic steering catheter whose turning radius depends on the length of flexible section and the constraints from inner walls of working space, the multi-point M-skin catheter can achieve various sets of steering by programming the easy magnetization axis of each coating section (FIG. 6C), leading to higher adaptability in implementing tasks in harsh environments. Taking a multi-point M-skin sampling cotton thread as an example (Supplementary Text), to better fit the irregular corner structure of a throat with sharp turn of ~90° and a narrow radius of ~10 mm, the thread was reprogrammed accordingly to angles of 90°, 30°, and 0° for the three sections, respectively. As the results show in FIG. 6D, the target-based reprogrammed cotton thread can achieve the fast directional steering under the action of magnetic torque and can reduce the risk of extrusion with throat wall during insertion as well. The ability to quickly set the desired orientation and designed configuration without changing the main structure of the catheter offers promising potentials for catheter manipulation in the complex esophagus, vessel, and urethra, where navigation is always required.

M-Skin-Covered Capsule for Active Delivery

An active drug delivery system demonstrates many advantages in disease treatment over traditional pills because of its higher local drug concentration and enhanced retention in the gastric mucous layer (33). Effective transportation of cargo containing drugs in multiple environments (dry, wet, flat, and pleated surface) would promote clinical applications. For instance, the stomach is relatively "dry" when empty but will become "wet" when full of food, water, and gastric juice. Moreover, if the lesion (e.g., stomach ulcer) is at the top of the stomach where liquid media cannot reach it easily due to gravity, a robot that can work at such environment could help. Compared with existing drug delivery systems (33-35), which are usually designed to work in liquid media (gastric juice and blood), our M-skin millirobot could achieve effective locomotion on different surfaces and in different media. That makes it a useful tool for the task in complex cavities, such as esophagus, stomach, and intestine. Moreover, the controllable disintegration property of the covered M-skin endows existing pills with an ability to release on demand, for instance, only releasing in the infection region rather than scattering randomly in the whole organ.

Figure 6E:
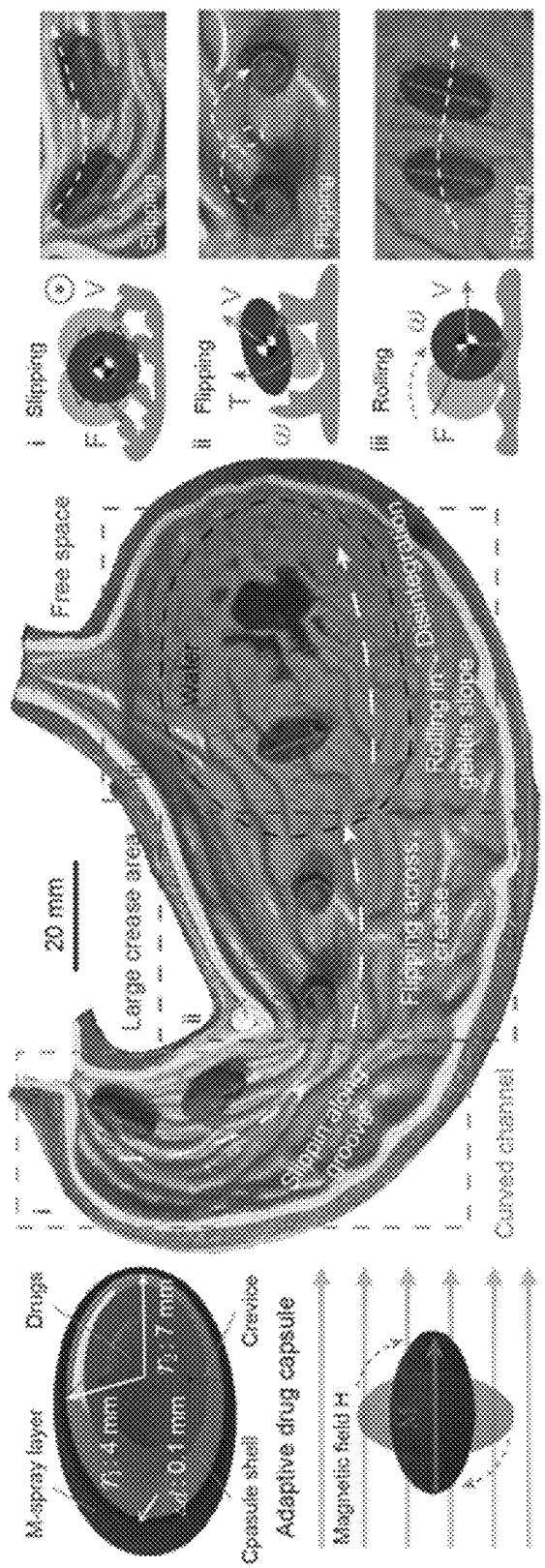
FIG. 6E schematically depicts the construction of an adaptive drug capsule millirobot and its multiple locomotion modes as well as controllable disintegration.
Figure 6F:
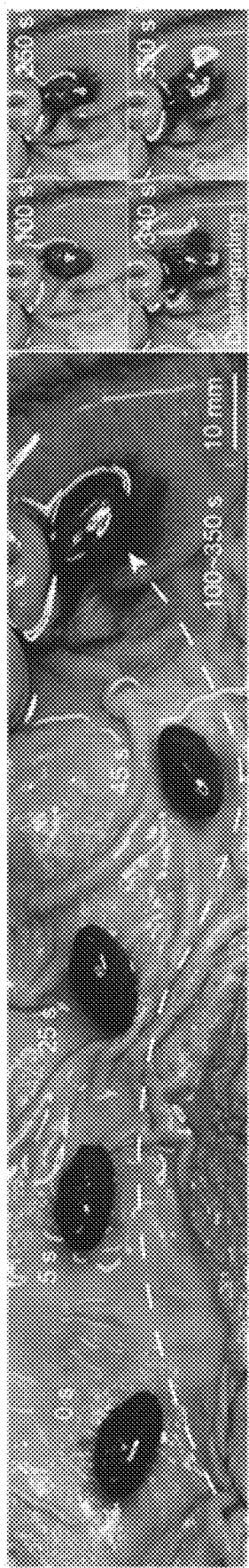
FIG. 6F shows controllable locomotion and disintegration of an as-fabricated M-skin capsule for active delivery in an ex vivo animal model.

To demonstrate the adaptive locomotion and controllable drug releasing ability, a nondeformable ellipsoidal capsule was converted into an M-skin millirobot by coating it with M-spray. The capsule shell was cut into two halves and agglutinated with M-spray to achieve controllable drug release by disintegrating the M-skin. As illustrated in FIG. 6E, the constructed adaptive drug capsule contains three layers in total, i.e., M-skin cover (thickness, ~100 μm), middle capsule shell (short axis, 8 mm; long axis, 14 mm), and the internal drugs (dyed by red stain Rhodamin 6G for visualization). Under the actuation of magnetic field, the constructed M-skin capsule was able to locomote at different modes including, but not limited to, slipping, flipping, and rolling, which correspond to the environment. For instance, the M-skin capsule could swing with a small amplitude of ~3 mm to decrease the friction from the ground, reach a motion speed of ~1 mm/s by adopting the longitudinal slipping motion along the groove of creases in the narrow curved channel (locomotion type i), flip across the staggered creases with a ~5 times higher speed than slipping in the large crease area (locomotion type ii), and roll with a ~10 times higher speed than slipping on the relatively open and flat space (locomotion type iii). Even challenged by the slippery surface and viscous resistance of the ropy gastric juice, the locomotion of M-skin capsule was still controllable and efficient (FIG. 6F). After reaching the target lesion, by applying the oscillating magnetic field (10 mT, 1 Hz), the connection between two halves of the capsule became unstable, and the drug (red stain) began to seep through the crevice.

In Vivo Demonstration in Rabbit Stomach Model

Figure 7A:
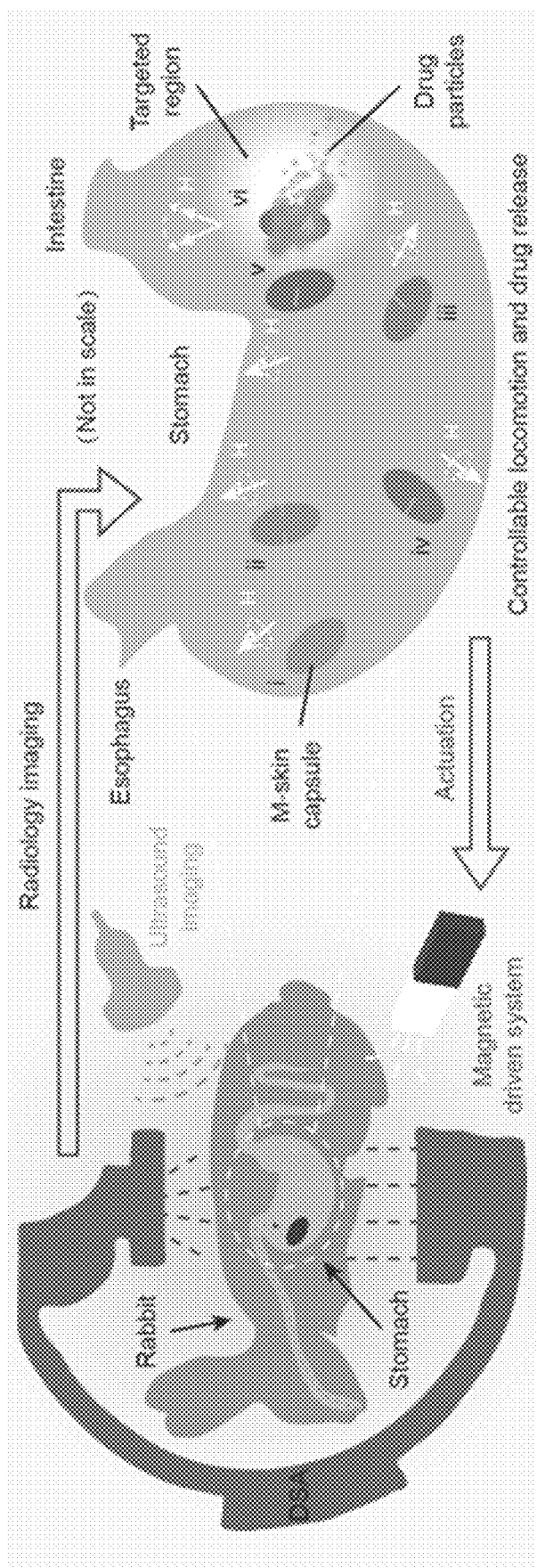
FIG. 7A schematically depicts an example of using the present invention for drug delivery in rabbit stomach, where the magnetic field is applied for robot actuation; radiology imaging is adopted for locomotion evaluation; and ultrasound imaging is adopted for drug release evaluation.

To further verify the feasibility and effectiveness of an M-spray-enabled millirobot for biomedical applications, an in vivo drug delivery test was conducted in the rabbit stomach using the M-skin capsule. As illustrated in FIG. 7A, the targeted region was set at the end of the stomach and close to the intestine. To demonstrate the drug delivery both in vivo (ultrasound imaging) and in vitro (cutting open stomach), microglass beads (500 μm) and biological stain (Indigo carmine, Phygene Scientific, PH9195) were encapsulated into the capsule. During the experiment, 1.0-g beads for control group 1 and 0.05-g biological stain for control group 2 were orally administered, whereas the M-skin capsule contained 1.0-g beads for experiment group 1 and 0.05-g biological stain for experiment group 2. These four rabbit groups underwent 8 hours of fasting treatment before the experiment, and water feeding and anesthesia were kept during the whole experiment process (Materials and Methods).

Figure 7B:
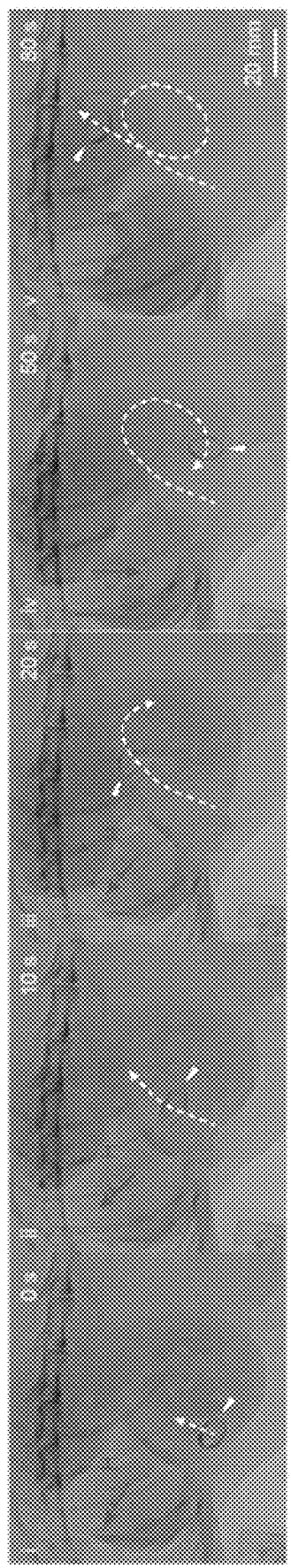
FIG. 7B shows a series of radiology images of an M-skin capsule according to an embodiment of the present invention steered in a stomach with a controllable O trajectory.
Figure 7C:
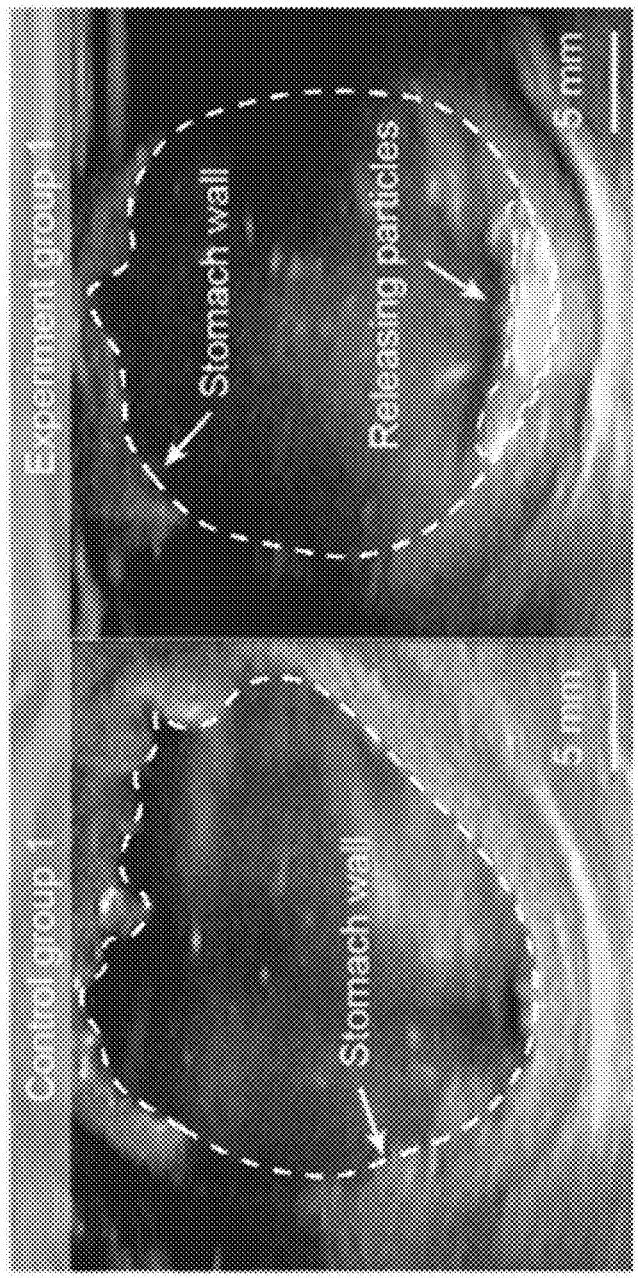
FIG. 7C shows ultrasound images for an in vivo evaluation of bead diffusion, where the distribution of beads released from the capsule in the rabbit stomach is sparse with limited detection in control group 1, whereas the bright region on the stomach wall in experiment group 1 indicates that the M-skin capsule can concentrate bead release on the targeted region.
Figure 7D:
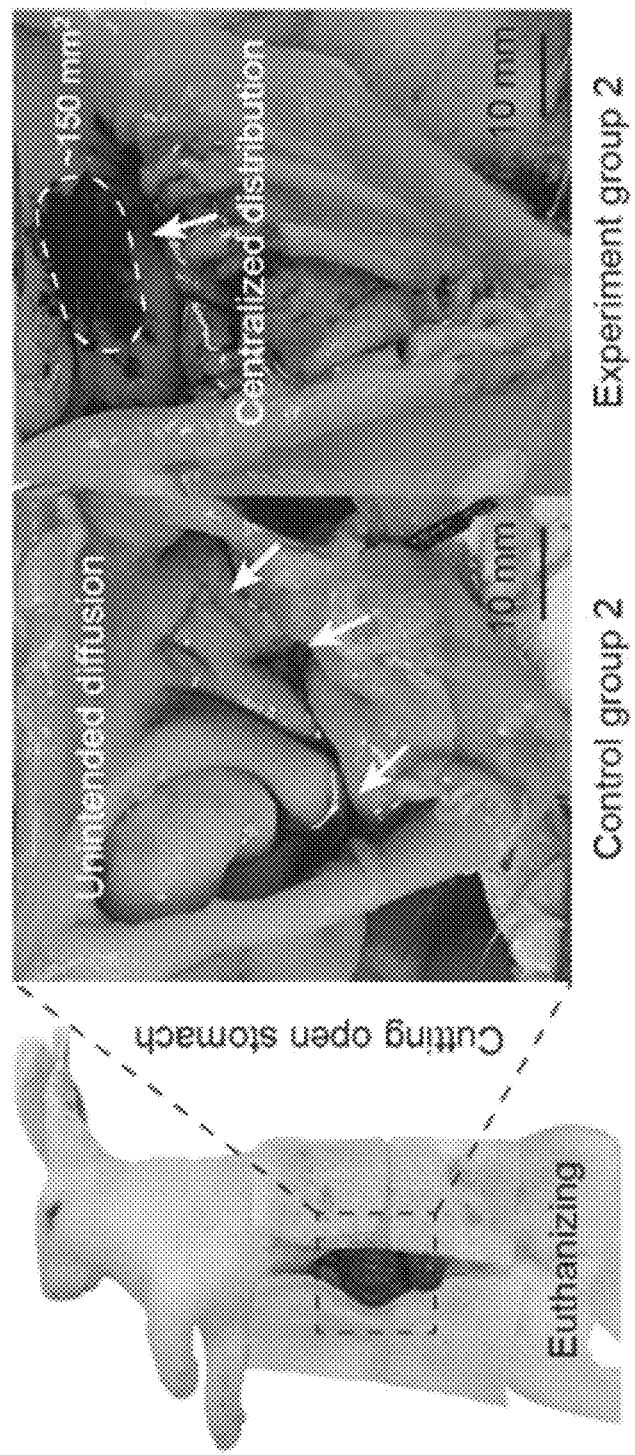
FIG. 7D shows optical images for the retention of biological stain in control group 2 (left) and experiment group 2 (right)
Figure 8A:
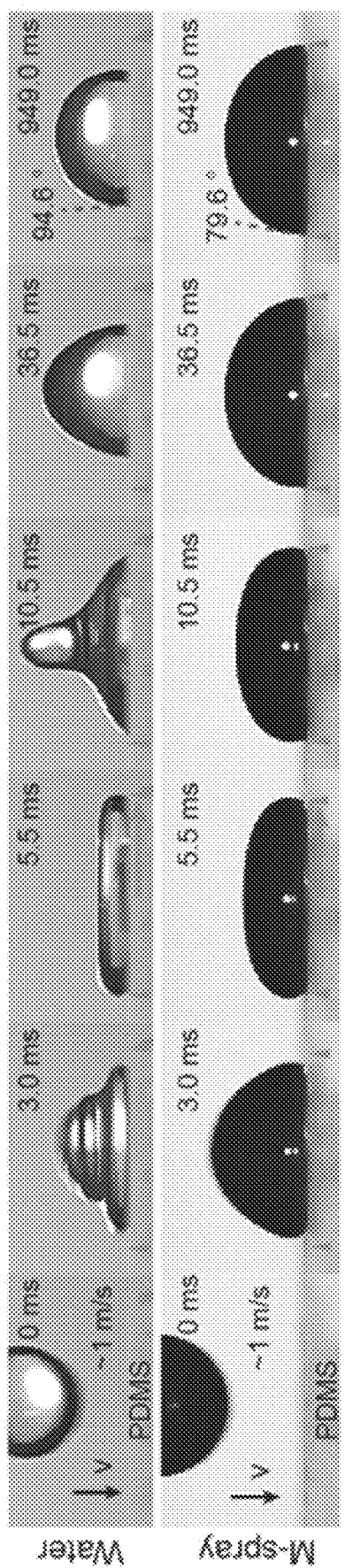
FIG. 8A and FIG. 8B show the comparison of adhesion property between water droplet and M-spray droplet.
Figure 8B:
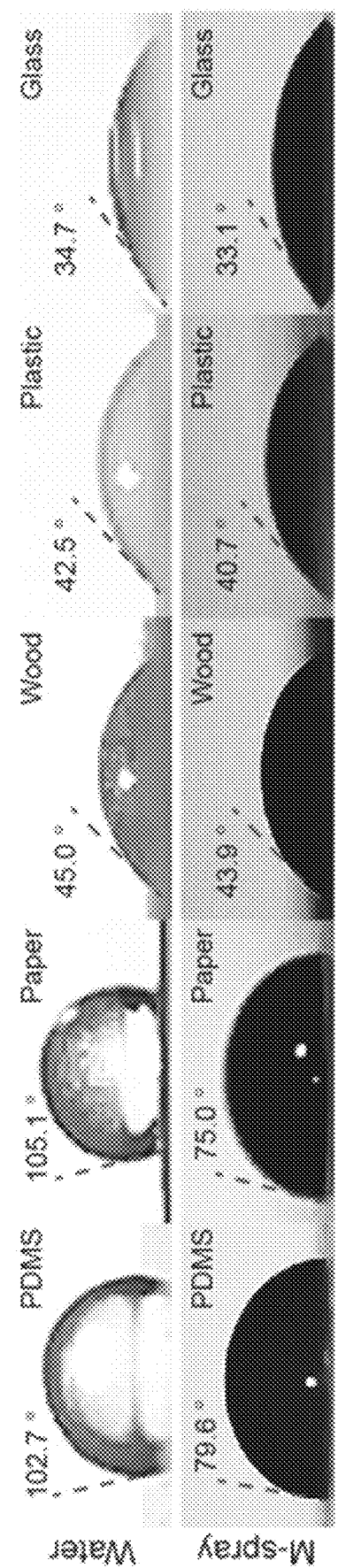

Owing to the covering of M-skin, the capsule in the stomach can be detected by radiology imaging [digital subtraction angiography (DSA), CGO-2100, Wandong], the position and orientation of which can then be used as a feedback for the robot actuation by magnetic field. As the time-lapse radiology images (from experiment group 1) in FIG. 7B show, the constructed M-skin capsule tolerated the ropy and the acid environment and achieved controllable locomotion with an "O" trajectory in the stomach. When the M-skin capsule approached the designed targeted region, the M-skin was disintegrated by applying the oscillating magnetic field to controllably release the encapsulated beads and stain. FIG. 7C gives the in vivo comparison results of the microbead release by ultrasound imaging. It indicates that the M-skin capsule can concentrate the beads' release on the targeted region, i.e., the bright region on the stomach wall, whereas the distribution of beads was almost sparse and could be hardly detected in control group 1. To further intuitively demonstrate the targeted diffusion and retention of drug, the beads were replaced by biological stain and repeated the control experiment with the same process. Then, the rabbits were euthanized, and their stomachs were collected to observe the distribution of biological stain after half an hour. As illustrated in FIG. 7D, comparing with the unintended diffusion in control group 2, the active drug delivery of M-skin capsule in experiment group 2 could effectively enhance the retention and the concentration of drug in specific lesions (~150 mm$^2$). These results suggest that the constructed M-skin capsule is feasible and effective for in vivo drug delivery.

DISCUSSION

Constructing a robot that can effectively adapt to different environments and interact with diverse objects is a grand challenge in robotics. Considering that target objects usually vary from each other in size, shape, and structure, it is challenging to develop an end effector or robot to handle all cases. Moreover, for the tasks in limited space, e.g., object transportation, the acceptable size increment superposed to the target is strictly limited, which raises higher demand for the robot design at small scale.

A simple fabrication process for on-demand milli-robots is therefore provided herein. The present invention leverages the adhesiveness and wetting ability of M-spray to turn a variety of milli-objects into millirobots regardless of the surface condition, e.g., flat or curve and hydrophilic or hydrophobic. Because the M-skin only accounts for a small volume ratio, it is able to preserve the original size, morphology, and structure of covered objects. Because the structure of an inanimate target is fully used for locomotion, the constructed robot demonstrates high working efficacy and loading ability, which can reach up to thousand-fold of its own volume and hundredfold of its own weight. Moreover, our millirobots are also reprogrammable and can demonstrate multimodal locomotion, thus enabling our robots to better adapt to various environments. Note that the M-spray is unharmful to the host owing to its disintegrable properties. The strategy of turning inanimate objects into moveable millirobots on demand can quickly realize the effective object operation, offering potentials for manipulation, transportation, and delivery in unpredictable, limited spaces.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

REFERENCES

The following is a list of references cited hereinabove:
1. Z. Zhakypov, K. Mori, K. Hosoda, J. Paik, Designing minimal and scalable insect-inspired multi-locomotion millirobots. *Nature* 571, 381-386 (2019).
2. M. Sitti, Miniature soft robots—road to the clinic. *Nature Reviews Materials* 3, 74 (2018).
3. K. Y. Ma, P. Chirarattananon, S. B. Fuller, R. J. Wood, Controlled flight of a biologically inspired, insect-scale robot. *Science* 340, 603-607 (2013).
4. X. Ji, X. Liu, V. Cacucciolo, M. Imboden, Y. Civet, A. El Haitami, S. Cantin, Y. Perriard, H. Shea, An autonomous untethered fast soft robotic insect driven by low-voltage dielectric elastomer actuators. *Science Robotics* 4, (2019).
5. M. Cianchetti, C. Laschi, A. Menciassi, P. Dario, Biomedical applications of soft robotics. *Nature Reviews Materials* 3, 143-153 (2018).
6. H. Xie, M. Sun, X. Fan, Z. Lin, W. Chen, L. Wang, L. Dong, Q. He, Reconfigurable magnetic microrobot swarm: Multimode transformation, locomotion, and manipulation. *Sci. Robot* 4, (2019)
7. Y. Chen, H. Zhao, J. Mao, P. Chirarattananon, E. F. Helbling, N. S. P. Hyun, D. R. Clarke, R. J. Wood, Controlled flight of a microrobot powered by soft artificial muscles. *Nature* 575, 324-329 (2019).
8. M. Lahikainen, H. Zeng, A. Priimagi, Reconfigurable photoactuator through synergistic use of photochemical and photothermal effects. *Nature communications* 9, 1-8 (2018).
9. A. Lendlein, Fabrication of reprogrammable shape-memory polymer actuators for robotics. *Science Robotics* 3, (2018).
10. W. Hu, G. Z. Lum, M. Mastrangeli, M. Sitti, Small-scale soft-bodied robot with multimodal locomotion. *Nature* 554, 81-85 (2018).
11. H. Lu, M. Zhang, Y. Yang, Q. Huang, T. Fukuda, Z. Wang, Y. Shen, A bioinspired multilegged soft millirobot that functions in both dry and wet conditions. *Nature communications* 9, 1-7 (2018).
12. S. Tottori, L. Zhang, F. Qiu, K. K. Krawczyk, A. Franco-Obregón, B. J. Nelson, Magnetic helical micromachines: fabrication, controlled swimming, and cargo transport. *Advanced materials* 24, 811-816 (2012).
13. S. D. de Rivaz, B. Goldberg, N. Doshi, K. Jayaram, J. Zhou, R. J. Wood, Inverted and vertical climbing of a quadrupedal microrobot using electroadhesion. *Science Robotics* 3, (2018).
14. Y. Wu, J. K. Yim, J. Liang, Z. Shao, M. Qi, J. Zhong, Z. Luo, X. Yan, M. Zhang, X. Wang, R. S. Fearing, Insect-scale fast moving and ultrarobust soft robot. *Science Robotics* 4, eaax1594 (2019).
15. Y. Zhang, B. K. Chen, X. Liu, Y. Sun, Autonomous robotic pick-and-place of microobjects. *IEEE Transactions on Robotics* 26, 200-207 (2009).
16. J. Hughes, U. Culha, F. Giardina, F. Guenther, A. Rosendo and F. Iida, Soft manipulators and grippers: a review. *Frontiers in Robotics and AI* 3, 69 (2016).
17. Z. Ren, W. Hu, X. Dong, M. Sitti, Multi-functional soft-bodied jellyfish-like swimming. *Nature communications* 10, 1-12 (2019).
18. H. Gu, Q. Boehler, H. Cui, E. Secchi, G. Savorana, C. De Marco, S. Gervasoni, Q. Peyron, T. Y. Huang, S. Pane, A. M. Hirt, Magnetic cilia carpets with programmable metachronal waves. *Nature communications* 11, 1-10 (2020).
19. H. W. Huang, F. E. Uslu, P. Katsamba, E. Lauga, M. S. Sakar, B. J. Nelson, Adaptive locomotion of artificial microswimmers. *Science advances* 5, caau 1532 (2019).
20. F. Ponton, C. Lebarbenchon, T. Lefèvre, D. G. Biron, D. Duneau, D. P. Hughes, F. Thomas, Parasite survives predation on its host. *Nature* 440, 756-756 (2006).
21. X. Chen, H. Yuk, J. Wu, C. S. Nabzdyk, X. Zhao, Instant tough bioadhesive with triggerable benign detachment. *Proceedings of the National Academy of Sciences* 117, 15497-15503 (2020).
22. S. Saito, S. Nobusue, E. Tsuzaka, C. Yuan, C. Mori, M. Hara, T. Seki, C. Camacho, S. Irle, S. Yamaguchi, Light-melt adhesive based on dynamic carbon frameworks in a columnar liquid-crystal phase. *Nature communications* 7, 12094 (2016).
23. G. Ju, M. Cheng, F. Guo, Q. Zhang, F. Shi, Elasticity-Dependent Fast Underwater Adhesion Demonstrated by Macroscopic Supramolecular Assembly. *Angewandte Chemie International Edition* 57, 8963-8967 (2018).
24. F. W. DelRio, M. P. de Boer, J. A. Knapp, E. D. Reedy, P. J. Clews, M. L. Dunn, The role of van der Waals forces in adhesion of micromachined surfaces. *Nature materials* 4, 629-634 (2005).
25. R. Hodge, G. H. Edward, G. P. Simon, Water absorption and states of water in semicrystalline poly(vinyl alcohol) films. *Polymer* 37, 1371-1376 (1996).
26. S. D'Amico, M. Hrabalova, U. Müller, E. Berghofer, Bonding of spruce wood with wheat flour glue—Effect of press temperature on the adhesive bond strength. *Industrial Crops and Products* 31, 255-260 (2010).
27. Y. Kim, H. Yuk, R. Zhao, S. A. Chester, X. Zhao, Printing ferromagnetic domains for untethered fast-transforming soft materials. *Nature* 558, 274-279 (2018).
28. W. Wang, J. Y. Lee, H. Rodrigue, S. H. Song, W. S. Chu, S. H. Ahn, Locomotion of inchworm-inspired robot made of smart soft composite (SSC). *Bioinspiration & biomimetics* 9, 046006 (2014).
29. J. Kim, S. E. Chung, S. E. Choi, H. Lee, J. Kim, S. Kwon, Programming magnetic anisotropy in polymeric microactuators. *Nature materials* 10, 747-752 (2011)
30. H. Markides, M. Rotherham, A. El Haj, Biocompatibility and toxicity of magnetic nanoparticles in regenerative medicine. *Journal of Nanomaterials* 2012, (2012).
31. Y. Kim, G. A. Parada, S. Liu, X. Zhao, Ferromagnetic soft continuum robots. *Science Robotics* 4, eaax7329 (2019).
32. V. N. Le, N. H. Nguyen, K. Alameh, R. Weerasooriya, P. Pratten, Accurate modeling and positioning of a magnetically controlled catheter tip. *Medical physics* 43, 650-663 (2016).

33. C. Chautems, A. Tonazzini, Q. Boehler, S. H. Jeong, D. Floreano, B. J. Nelson, Magnetic continuum device with variable stiffness for minimally invasive surgery. *Advanced Intelligent Systems* 2, 1900086 (2020).
34. B. E. F. de Ávila, P. Angsantikul, J. Li, M. A. Lopez-Ramirez, D. E. Ramírez-Herrera, S. Thamphiwatana, C. Chen, J. Delezuk, R. Samakapiruk, V. Ramez, M. Obonyo, Micromotor-enabled active drug delivery for in vivo treatment of stomach infection. *Nature communications* 8, 1-9 (2017).
35. Y. Alapan, U. Bozuyuk, P. Erkoc, A. C. Karacakol, M. Sitti, Multifunctional surface microrollers for targeted cargo delivery in physiological blood flow. *Science Robotics* 5, (2020).

The invention claimed is:

1. A method of fabricating one or more robots from one or more inanimate objects of one-dimensional to three-dimensional configurations on-demand, comprising:
splashing a self-adhesive, viscous and wettable spray composition in one or more splashing regions on a surface of a substrate of the one or more inanimate objects at room temperature, wherein areas other than the splashing regions on the surface of the substrate are masked if there is more than one splashing region, and wherein the composition comprises:
one or more curable adhesive materials; and
a plurality of drivable materials,
the one or more curable adhesive materials, upon exposure to one or more stimuli, forming a viscous paste to splash in one or more splashing regions on a surface of a substrate with which the composition is in contact, and after said composition being cured, further increasing mechanical strength of the cured composition while preventing detachment of the cured composition from said substrate; and
the plurality of drivable materials, upon exposure to one or more stimuli and prior to curing of the composition, being aligned to have an oriented actuation direction either perpendicularly to a deformable direction of the one or more robots or in parallel to a longest planar axis of a drivable thin film formed on the substrate surface from the cured composition;
applying an initial stimuli to the composition to align the one or more drivable materials to have an oriented actuation direction parallel to the direction of the applied initial stimuli;
curing the composition to form the drivable thin film with an oriented actuation direction either perpendicular to a deformable direction of the one or more robots or parallel to a longest planar axis of the drivable thin film,
wherein for the substrate surface with more than one splashing region the one or more robots are obtained by repeating said splashing, applying the initial stimuli to the composition, and curing the composition until all the splashing regions are cured followed by cutting the unmasked areas out from the substrate,
wherein the composition comprises a first adhesive polymer, the one or more drivable materials including a plurality of magnetic responsive particle, and a second adhesive polymer; wherein the first adhesive polymer, the plurality of magnetic responsive particles and the second adhesive polymer are in mass ratio of 1:8:11 in the composition.

2. The method of claim 1, wherein the first adhesive polymer and the plurality of magnetic-responsive particles are doped into a solution of the second adhesive polymer at room temperature, followed by atomization into droplets for forming a thin film on the substrate of the inanimate objects.

3. The method of claim 2, wherein the first adhesive polymer is gluten.

4. The method of claim 2, wherein the magnetic-responsive particles are iron particles.

5. The method of claim 2, wherein the second adhesive polymer is polyvinyl alcohol.

6. The method of claim 1, wherein the substrate comprises polydimethylsiloxane, glass, paper, plastic, and wood, and wherein the surface of the substrate is flat, curved, or irregular.

7. The method of claim 1, wherein one of the stimuli is a magnetic field in a magnitude of about 100 to 200 mT.

* * * * *